US012116620B2

(12) United States Patent
Majlessi et al.

(10) Patent No.: US 12,116,620 B2
(45) Date of Patent: Oct. 15, 2024

(54) COMPOSITIONS AND METHODS FOR DETECTING OR QUANTIFYING PARAINFLUENZA VIRUS

(71) Applicant: Gen-Probe Incorporated, San Diego, CA (US)

(72) Inventors: Mehrdad Majlessi, Escondido, CA (US); Pamela Douglass, Kansas City, MO (US); Daniel Kolk, Ramona, CA (US)

(73) Assignee: Gen-Probe Incorporated, San Diego, CA (US)

( * ) Notice: Subject to any disclaimer, the term of this patent is extended or adjusted under 35 U.S.C. 154(b) by 448 days.

(21) Appl. No.: 17/072,890

(22) Filed: Oct. 16, 2020

(65) Prior Publication Data

US 2021/0040541 A1  Feb. 11, 2021

Related U.S. Application Data

(62) Division of application No. 15/934,273, filed on Mar. 23, 2018, now Pat. No. 10,844,425.

(60) Provisional application No. 62/476,435, filed on Mar. 24, 2017.

(51) Int. Cl.
C12Q 1/68 (2018.01)
C12Q 1/6811 (2018.01)
C12Q 1/6816 (2018.01)
C12Q 1/6851 (2018.01)
C12Q 1/6853 (2018.01)
C12Q 1/686 (2018.01)
C12Q 1/6876 (2018.01)
C12Q 1/6888 (2018.01)
C12Q 1/70 (2006.01)

(52) U.S. Cl.
CPC .......... *C12Q 1/6811* (2013.01); *C12Q 1/6816* (2013.01); *C12Q 1/6851* (2013.01); *C12Q 1/6853* (2013.01); *C12Q 1/686* (2013.01); *C12Q 1/6876* (2013.01); *C12Q 1/6888* (2013.01); *C12Q 1/701* (2013.01); *C12Q 2600/118* (2013.01); *C12Q 2600/166* (2013.01)

(58) Field of Classification Search
CPC .............. C12Q 1/701; C12Q 2600/166; C12Q 2600/118
See application file for complete search history.

(56) References Cited

U.S. PATENT DOCUMENTS

| | | |
|---|---|---|
| 5,744,299 A | 4/1998 | Henrickson et al. |
| 6,015,664 A | 1/2000 | Henrickson et al. |
| 2003/0050470 A1* | 3/2003 | An .................. C07H 21/00 435/6.14 |
| 2004/0023207 A1* | 2/2004 | Polansky ............. A61K 48/005 435/456 |
| 2007/0259337 A1 | 11/2007 | Hully et al. |
| 2011/0077170 A1 | 3/2011 | Lina et al. |
| 2013/0157874 A1 | 6/2013 | Dowd |
| 2014/0127671 A1* | 5/2014 | Yoo ........................ C12Q 1/701 435/5 |

FOREIGN PATENT DOCUMENTS

| | | |
|---|---|---|
| CN | 101550455 A | 10/2009 |
| CN | 101985665 A | 3/2011 |
| CN | 102115795 A | 7/2011 |
| CN | 104059996 | 9/2014 |
| CN | 105734168 A | 7/2016 |
| EP | 1201768 | 5/2002 |
| JP | 2005528891 A | 9/2005 |
| JP | 2007129923 A | 5/2007 |
| JP | 2009045070 A | 3/2009 |
| JP | 2009517087 A | 4/2009 |
| JP | 2014505704 A | 3/2014 |
| JP | 2015506666 A | 3/2015 |
| RU | 2515911 C1 | 5/2014 |
| WO | 9716570 | 5/1997 |
| WO | 2003080638 A2 | 10/2003 |
| WO | 2007064758 A2 | 6/2007 |
| WO | 2007087336 A2 | 8/2007 |
| WO | 2012106508 A1 | 8/2012 |
| WO | 2013049891 A1 | 4/2013 |

OTHER PUBLICATIONS

Almajhdi FN. Hemagglutinin-neuraminidase gene sequence-based reclassification of human parainfluenza virus 3 variants. Intervirology. 2015; 58(1):35-40. Epub Jan. 13, 2015. (Year: 2015).*
Cordey et al., 2009. Simultaneous detection of parainfluenza viruses 1 and 3 by real-time reverse transcription-polymerase chain reaction. Journal of virological methods, 156(1-2), pp. 166-168. (Year: 2009).*
Genbank Accession No. AB012132 Human respirovirus 3 genomic RNA, complete sequence, viral complementary strand (submitted Mar. 12, 1998, retrieved on Mar. 7, 2023 from http://www.ncbi.nlm.nih.gov/nuccore/AB012132). (Year: 1998).*
Genbank Accession No. AF213352 Human parainfluenza virus 2 hemagglutinin-neuraminidase glycoprotein (HN) mRNA, complete cds (submitted Dec. 8, 1999, retrieved on Sep. 11, 2019 from http://www.ncbi.nlm.nih.gov/nuccore/AF213352). (Year: 1999).*

(Continued)

*Primary Examiner* — Stephanie K Mummert
*Assistant Examiner* — Olayinka A Oyeyemi
(74) *Attorney, Agent, or Firm* — Christensen O'Connor Johnson Kindness PLLC; Jeffrey E. Landes

(57) ABSTRACT

Compositions, methods, kits, and uses are provided for detecting or quantifying an Human Parainfluenza virus 1 (HPIV-1), HPIV-2, HPIV-3, and/or HPIV-4 nucleic acid, e.g., using nucleic acid amplification and hybridization assays. In some embodiments, the compositions, methods, kits, and uses target the HN gene of HPIV-1, HPIV-2, and/or HPIV-3 and/or the NP gene of HPIV-4.

17 Claims, No Drawings

Specification includes a Sequence Listing.

(56) References Cited

OTHER PUBLICATIONS

Genbank Accession No. GU732171 Human parainfluenza virus 3 strain BJ/341/09 hemagglutinin-neuraminidase (HN) gene, complete cds (submitted Feb. 10, 2010, retrieved on Sep. 11, 2019 from http://www.ncbi.nlm.nih.gov/nuccore/GU732171). (Year: 2010).*
Genbank Accession No. JN089925 Human parainfluenza virus 1 strain Oklahoma/4409/2010 hemagglutinin-neuraminidase mRNA, complete cds (submitted Jun. 7, 2011, retrieved on Sep. 11, 2019 from http://www.ncbi.nlm.nih.gov/nuccore/JN089925). (Year: 2011).*
Genbank Accession No. KF908238 Human parainfluenza virus 4b strain QLD-01, complete genome (submitted Nov. 26, 2013, retrieved on Sep. 11, 2019 from http://www.ncbi.nlm.nih.gov/nuccore/KF908238). (Year: 2013).*
Genbank Accession No. NC_001796 Human parainfluenza virus 3, complete genome (submitted Dec. 5, 2000, retrieved on Mar. 7, 2023 from http://www.ncbi.nlm.nih.gov/nuccore/NC_001796). (Year: 2005).*
Echevarria et al., 1998. Simultaneous detection and identification of human parainfluenza viruses 1, 2, and 3 from clinical samples by multiplex PCR. Journal of Clinical Microbiology, 36(5), pp. 1388-1391. (Year: 1998).*
Hu et al. Development of a real-time RT-PCR assay for detection and quantitation of parainfluenza virus 3. J Virol Methods 2005; 130:145-8. (Year: 2005).*
Jansen et al., Development and evaluation of a four-tube real time multiplex PCR assay covering fourteen respiratory viruses, and comparison to its corresponding single target counterparts. Journal of Clinical Virology. Jul. 1, 2011; 51(3):179-85. (Year: 2011).*
Ji et al., 2012. Simultaneous detection of human parainfluenza viruses 1, 2, 3 by multiplex real-time reverse transcription-polymerase chain reaction with LNA probes. Chinese Journal of Experimental and Clinical Virology, 26(5), pp. 388-390. (Year: 2012).*
Jin et al., Examination of the specificity of DNA methylation profiling techniques towards 5-methylcytosine and 5-hydroxymethylcytosine. Nucleic Acids Res. Jun. 2010; 8(11), e125, pp. 1-7. Epub Apr. 5, 2010. (Year: 2010).*
Mao et al., 2012. Human parainfluenza virus-associated respiratory tract infection among children and genetic analysis of HPIV-3 strains in Beijing, China. (Year: 2012).*
Ono et al., Synthesis of decadeoxyribonucleotides containing N 6-methyladenine, N 4-methylcytosine, and 5-methylcytosine: recognition and cleavage by restriction endonucleases (nucleosides and nucleotides part 74). Nucleic acids research. Jan. 12, 1987; 15(1):219-32. (Year: 1987).*
Ramezannia et al., 2016. Development of a multiplex real-time RT-PCR assay for detection of human parainfluenza viruses in patients with respiratory symptoms. Future Virology, 11(9), pp. 611-617. (Year: 2016).*
SantaLucia Jr, John. Physical principles and visual-OMP software for optimal PCR design. PCR Primer Design. Humana Press, 2007: pp. 3-33. (Year: 2007).*
Gadberry et al., 2005. Primaclade—a flexible tool to find conserved PCR primers across multiple species. Bioinformatics, 21(7), pp. 1263-1264. (Year: 2005).*
Genbank Accession No. M32982, Parainfluenza virus type 4A nucleocapsid (NP) mRNA, complete cds (submitted Aug. 2, 1993, retrieved on Jul. 15, 2023 from http://www.ncbi.nlm.nih.gov/nuccore/M32982). (Year: 1993).*
Genbank Accession No. KF908238—Human parainfluenza virus 4b strain QLD-01, complete genome, submitted by Nov. 26, 2013, retrieved on Aug. 22, 2024 from http://www.ncbi.nlm.nih.gov/nuccore/KF908238). (Year: 2013).*
Chakravorty, et al. "Rapid Universal Identification of Bacterial Pathogens from Clinical Cultures by Using a Novel Sloppy Molecular Beacon Melting Temperature Signature Technique," Journal of Clinical Microbiology, 48(1): 258-267 (2010).
Gresham, et al. "Optimized detection of sequence variation in heterozygous genomes using DNA microarrays with isothermal-melting probes," Proceedings of the National Academy of Sciences, 107(4): 1482-1487 (2010).
Almajhdi "Hemagglutinin-neuraminidase gene sequence-based reclassification of human parainfluenza virus 3 variants." Intervirology. 2015; 58(1):35-40. Epub Jan. 13, 2015. (Year: 2015).
Bellau-Pujol et al., "Development of three multiplex RT-PCR assays for the detection of 12 respiratory RNA viruses." J. Viral. Methods 126: 53-63. (2005).
GenBank Accession No. AF213352 Human parainfluenza virus 2 hemagglutinin-neuraminidase glycoprotein (H N) mRNA, complete eds (submitted Dec. 8, 1999, retrieved on Sep. 11, 2019 from http://www.ncbi.nlm.nih.gov/nuccore/AF213352). (Year: 1999).
Santalucia Jr, John. "Physical principles and visual-OMP software for optimal PCR design. PCR Primer Design," Humana Press, pp. 3-33. (2007).
GenBank Accession No. JN089925 Human parainfluenza virus 1 strain Oklahoma/4409/2010 hemagglutinin-neuraminidase mRNA, complete eds (submitted Jun. 7, 2011, retrieved on Sep. 11, 2019 from http://www.ncbi.nlm.nih.gov/nuccore/JN089925). (Year: 2011).
Hu et al., "Rappaport R, et al. Development of a real-time RT-PCR assay for detection and quantitation of parainfluenza virus 3." J Viral Methods 130: 145-148 (2005).
Jansen et al. "Development and evaluation of a four-tube real time multiplex PCR assay covering fourteen respiratory viruses, and comparison to its corresponding single target counterparts." J Clin Viral., 51 (3): 179-85. Epub May 14, 2011 (2011).
Ji et al. "Simultaneous detection of human parainfluenza viruses 1, 2, 3 by multiplex real-time RT-PCR with LNA probes." Zhonghua shi yan he lin chuang bing du xue za zhi=Zhonghua shiyan he linchuang bingduxue zazhi=Chinese journal of experiment and clinical virology, 26(5):388-90. (2012).
Jin, et al., "Examination of the specificity of DNA methylation profiling techniques towards 5-methylcytosine and 5-hydroxymethylcytosine," Nucleic Acids Res. Jun. 2010; 8(11):e125. Epub Apr. 5, 2010. (Year: 2010).
Mizuta et al. Detailed genetic analysis of hemagglutinin-neuraminidase glycoprotein gene in human parainfluenza virus type 1 isolates from patients with acute respiratory infection between 2002 and 2009 in Yamagata prefecture, Japan. Viral Journal, 8:533. pp 1-9. (2011).
Mizuta et al., "Molecular evolution of the haemagglutinin-neuraminidase gene in human parainfluenza virus type 3 isolates from children with acute respiratory illness in Yamagata prefecture," Japan. J Med Microbial. Apr. 2014; 63(Pt 4):570-7. Epub Jan. 25, 2014 . (Year. 2014).
PCT International Search Report, International Application No. PCT/US2018/024021, Aug. 21, 2018.
PCT Invitation to Pay Additional Fees, Partial International Search Report, and Provisional Written Opinion, International Application No. PCT/US2018/024021, Jun. 25, 2018.
PCT Written Opinion, International Application No. PCT/US2018/024021, Aug. 21, 2018.
Loeffelholz, "Towards Improved Accuracy of Bordetella pertussis Nucleic Acid Amplification Tests," Journal of Clinical Microbiology, 50(7): 2186-2190 (2012).
Wiemer et al., "Real-time multiplex PCR for simultaneous detection of *Campylobacter jejuni, Salmonella, Shigella* and *Yersinia* species in fecal samples," International Journal of Medical Microbiology, 301: 577-584 (2011).
Japanese Notice of Reasons for Rejection as mailed on Aug. 4, 2023, issued in corresponding Japanese Application No. 2022-116624, filed Mar. 23, 2018, 14 pages.
Extended European Search Report dated Jan. 25, 2024 from corresponding European Application No. 23199444.3.
Prosnyak et al., "Substitution 2-Aminodenine and 5-Methylcytosine for Adenine and Cytosine in Hybridization Probes Increases the Sensitivity of DNA Fingerprinting", Geonomics, vol. 21, Jan. 1, 1994, pp. 490-494.

* cited by examiner

COMPOSITIONS AND METHODS FOR DETECTING OR QUANTIFYING PARAINFLUENZA VIRUS

This application is a divisional application of U.S. Application Ser. No. 15/934,273, filed Mar. 23, 2018, which claims the benefit of US Provisional Patent Application No. 62/476,435, filed Mar. 24, 2017, each of which are incorporated herein by reference for all purposes.

The embodiments herein are directed to the field of detecting infectious agents, more specifically by using compositions and methods to detect viruses including Human Parainfluenza Viruses 1, 2, 3, and 4 (HPIV-1, HPIV-2, HPIV-3, and HPIV-4).

Human Parainfluenza Viruses are members of the Paramyxoviridae family and are negative-sense, single-stranded RNA viruses. HPIV types 1-4 have been identified, with type 4 containing subtypes 4a and 4b. HPIVs can cause cold-like symptoms, respiratory tract illnesses, croup (especially HPIV-1 and 2), and bronchiolitis, bronchitis, and/or pneumonia (especially HPIV-3). HPIVs are spread in modes common to respiratory viruses, such as through the air including by coughing or sneezing, through close personal contact including handshakes or other touching, or through touching objects or surfaces exposed to the virus.

There are no known vaccines or specific antiviral treatment for HPIV infections, but symptoms can be managed. Given the variety of symptoms that can be caused by HPIV and their similarity to other respiratory infections such as colds, influenza, and bacterial pneumonia, it is important to rapidly identify HPIV infections as such to facilitate appropriate treatments and avoid administering unnecessary or ineffective medications.

Nucleic acid-based detection techniques, including amplification-based approaches, e.g., TaqMan™ RT-PCR, provide rapid detection and quantification of HPIVs. However, the heterogeneity of HPIV sequences across and within the various types and subtypes can cause difficulties with the sensitivity and/or specificity of such techniques. Accordingly, there is a need for compositions and methods that allow sensitive and specific detection and quantification of HPIVs. This disclosure aims to meet these needs, provide other benefits, or at least provide the public with a useful choice.

Accordingly, provided herein is a composition or kit comprising at least first and second amplification oligomers, wherein: the first amplification oligomer and second amplification oligomer are configured to amplify an HPIV-3 amplicon of at least about 50 nucleotides in length comprising at least one Human Parainfluenza Virus 3 (HPIV-3) position located in the range of positions 1295-1305, 1350-1360, and/or 1380-1390.

Also provided herein is a composition or kit comprising at least first and second amplification oligomers, wherein: (a) the first amplification oligomer is configured to hybridize to a site comprising HPIV-3 position 1270 and the second amplification oligomer is configured to hybridize to a site comprising HPIV-3 position 1355, and the first and second amplification oligomers are configured to produce an HPIV-3 amplicon; or (b) the first amplification oligomer is configured to hybridize to a site comprising HPIV-3 position 1355 and the second amplification oligomer is configured to hybridize to a site comprising HPIV-3 position 1437, and the first and second amplification oligomers are configured to produce an HPIV-3 amplicon.

Also provided herein is a method of detecting HPIV-3 in a sample, comprising: contacting the sample with at least first and second amplification oligomers, thereby forming a composition, performing a nucleic acid amplification reaction in the composition which produces an HPIV-3 amplicon of at least about 50 nucleotides in length in the presence of an HPIV-3 nucleic acid, and detecting the presence or absence of the at least one amplicon, wherein: the first amplification oligomer and second amplification oligomer are configured to amplify an HPIV-3 amplicon comprising at least one Human Parainfluenza Virus 3 (HPIV-3) position located within positions 1295-1305, 1350-1360, and/or 1380-1390.

Also provided herein is a method of detecting HPIV-3 in a sample, comprising: contacting the sample with at least first and second amplification oligomers, thereby forming a composition, performing a nucleic acid amplification reaction in the composition which produces an HPIV-3 amplicon in the presence of an HPIV-3 nucleic acid, and detecting the presence or absence of the at least one amplicon, wherein:

(a) the first amplification oligomer is configured to hybridize to a site comprising HPIV-3 position 1270 and the second amplification oligomer is configured to hybridize to a site comprising HPIV-3 position 1355, and the first and second amplification oligomers are configured to produce an HPIV-3 amplicon; or (b) the first amplification oligomer is configured to hybridize to a site comprising HPIV-3 position 1355 and the second amplification oligomer is configured to hybridize to a site comprising HPIV-3 position 1437, and the first and second amplification oligomers are configured to produce an HPIV-3 amplicon.

In some embodiments, the amplicon comprises HPIV-3 position 1305. In some embodiments, the amplicon comprises HPIV-3 position 1355. In some embodiments, the amplicon comprises HPIV-3 position 1380.

In some embodiments, the first oligomer competes for hybridization to an HPIV-3 nucleic acid under stringent conditions with an oligomer having a sequence consisting of SEQ ID NO: 25. In some embodiments, the first oligomer comprises the sequence of SEQ ID NO: 25 with up to two mismatches. In some embodiments, the first oligomer comprises the sequence of SEQ ID NO: 25.

In some embodiments, the second oligomer competes for hybridization to an HPIV-3 nucleic acid under stringent conditions with an oligomer having a sequence consisting of SEQ ID NO: 36. In some embodiments, wherein the second oligomer comprises the sequence of SEQ ID NO: 36 with up to two mismatches. In some embodiments, wherein the second oligomer comprises the sequence of SEQ ID NO: 36.

In some embodiments, wherein the first oligomer competes for hybridization to an HPIV-3 nucleic acid under stringent conditions with an oligomer having a sequence consisting of SEQ ID NO: 28. In some embodiments, wherein the first oligomer comprises the sequence of SEQ ID NO: 28 with up to two mismatches. In some embodiments, wherein the first oligomer comprises the sequence of SEQ ID NO: 28.

In some embodiments, wherein the second oligomer competes for hybridization to an HPIV-3 nucleic acid under stringent conditions with an oligomer having a sequence consisting of SEQ ID NO: 37. In some embodiments, wherein the second oligomer comprises the sequence of SEQ ID NO: 37 with up to two mismatches. In some embodiments, wherein the second oligomer comprises the sequence of SEQ ID NO: 37.

In some embodiments, the first oligomer comprises at least one 5-methylcytosine residue. In some embodiments, at least about half of the C residues in the first oligomer are 5-methylated. In some embodiments, substantially all of the C residues in the first oligomer are 5-methylated. In some embodiments, the second oligomer comprises at least one 5-methylcytosine. In some embodiments, at least about half of the C residues in the second oligomer are 5-methylated. In some embodiments, substantially all of the C residues in the second oligomer are 5-methylated.

In some embodiments, a composition or kit disclosed herein further comprises a third oligomer configured to hybridize to the amplicon, and the third oligomer comprises a detectable label. In some embodiments of a method disclosed herein, the presence or absence of the amplicon is detected according to the occurrence or non-occurrence of hybridization of the third oligomer to the amplicon.

In some embodiments of a method disclosed herein, an HPIV-3 nucleic acid is quantified by monitoring production of the HPIV-3 amplicon.

In some embodiments, the third oligomer competes for hybridization to an HPIV-3 nucleic acid under stringent conditions with an oligomer having a sequence consisting of SEQ ID NO: 31, 32, 33, 34, or 35. In some embodiments, the third oligomer comprises the sequence of SEQ ID NO: 31 with up to two mismatches. In some embodiments, the third oligomer comprises the sequence of SEQ ID NO: 31. In some embodiments, the third oligomer comprises the sequence of SEQ ID NO: 32 with up to two mismatches. In some embodiments, the third oligomer comprises the sequence of SEQ ID NO: 32. In some embodiments, the third oligomer comprises the sequence of SEQ ID NO: 33 with up to two mismatches. In some embodiments, the third oligomer comprises the sequence of SEQ ID NO: 33. In some embodiments, the third oligomer comprises the sequence of SEQ ID NO: 34 with up to two mismatches. In some embodiments, the third oligomer comprises the sequence of SEQ ID NO: 34. In some embodiments, the third oligomer comprises the sequence of SEQ ID NO: 35 with up to two mismatches. In some embodiments, the third oligomer comprises the sequence of SEQ ID NO: 35.

In some embodiments, the third oligomer competes for hybridization to an HPIV-3 nucleic acid under stringent conditions with an oligomer having a sequence consisting of SEQ ID NO: 26, 27, 28, 29, or 30. In some embodiments, the third oligomer comprises the sequence of SEQ ID NO: 26 with up to two mismatches. In some embodiments, the third oligomer comprises the sequence of SEQ ID NO: 26. In some embodiments, the third oligomer comprises the sequence of SEQ ID NO: 27 with up to two mismatches. In some embodiments, the third oligomer comprises the sequence of SEQ ID NO: 27. In some embodiments, the third oligomer comprises the sequence of SEQ ID NO: 28 with up to two mismatches. In some embodiments, the third oligomer comprises the sequence of SEQ ID NO: 28. In some embodiments, the third oligomer comprises the sequence of SEQ ID NO: 29 with up to two mismatches. In some embodiments, the third oligomer comprises the sequence of SEQ ID NO: 29.

In some embodiments, the third oligomer comprises at least one 5-methylcytosine. In some embodiments, at least about half of the C residues in the third oligomer are 5-methylated. In some embodiments, substantially all of the C residues in the third oligomer are 5-methylated.

In some embodiments, the composition or kit further comprises a fourth oligomer different from the third oligomer, and the fourth oligomer is configured to hybridize to the amplicon and comprises a detectable label. In some embodiments, the fourth oligomer comprises the sequence of SEQ ID NO: 31, 32, 33, 34, or 35. In some embodiments, the fourth oligomer comprises the sequence of SEQ ID NO: 26, 27, 28, 29, or 30. In some embodiments, the fourth oligomer comprises at least one 5-methylcytosine. In some embodiments, at least about half of the C residues in the fourth oligomer are 5-methylated. In some embodiments, substantially all of the C residues in the fourth oligomer are 5-methylated.

In some embodiments, a composition or kit disclosed herein further comprises a first Human Parainfluenza Virus 1 (HPIV-1) amplification oligomer and a second HPIV-1 amplification oligomer, wherein: the first HPIV-1 amplification oligomer and second HPIV-1 amplification oligomer are configured to amplify an HPIV-1 amplicon of at least about 50 nucleotides in length comprising at least one HPIV-1 position located within HPIV-1 positions 330-490 or 960-1100.

Also provided herein is a composition or kit comprising at least a first HPIV-1 amplification oligomer and a second HPIV-1 amplification oligomer, wherein: the first HPIV-1 amplification oligomer and second HPIV-1 amplification oligomer are configured to amplify an HPIV-1 amplicon of at least about 50 nucleotides in length comprising at least one HPIV-1 position located within HPIV-1 positions 330-490 or 960-1100.

Also provided herein is a method of detecting HPIV-1 in a sample, comprising: contacting the sample with at least first and second amplification oligomers, thereby forming a composition, performing a nucleic acid amplification reaction in the composition which produces an HPIV-1 amplicon in the presence of an HPIV-1 nucleic acid, and detecting the presence or absence of the at least one amplicon, wherein: the first HPIV-1 amplification oligomer and second HPIV-1 amplification oligomer are configured to amplify an HPIV-1 amplicon of at least about 50 nucleotides in length comprising at least one HPIV-1 position located within HPIV-1 positions 330-490 or 960-1100.

In some embodiments, the first HPIV-1 amplification oligomer is configured to hybridize to a site comprising HPIV-1 position 970 and the second HPIV-1 amplification oligomer is configured to hybridize to a site comprising HPIV-1 position 1098.

In some embodiments, the first HPIV-1 amplification oligomer competes for hybridization to an HPIV-1 nucleic acid under stringent conditions with an oligomer having a sequence consisting of SEQ ID NO: 6. In some embodiments, the first HPIV-1 oligomer comprises the sequence of SEQ ID NO: 6 with up to two mismatches. In some embodiments, the first HPIV-1 oligomer comprises the sequence of SEQ ID NO: 6.

In some embodiments, the second HPIV-1 amplification oligomer competes for hybridization to an HPIV-1 nucleic acid under stringent conditions with an oligomer having a sequence consisting of SEQ ID NO: 24. In some embodiments, the second HPIV-1 oligomer comprises the sequence of SEQ ID NO: 24 with up to two mismatches. In some embodiments, the second HPIV-1 oligomer comprises the sequence of SEQ ID NO: 24.

In some embodiments, the first HPIV-1 amplification oligomer is configured to hybridize to a site comprising HPIV-1 position 331 and the second HPIV-1 amplification oligomer is configured to hybridize to a site comprising HPIV-1 position 486.

In some embodiments, the first HPIV-1 amplification oligomer competes for hybridization to an HPIV-1 nucleic acid under stringent conditions with an oligomer having a sequence consisting of SEQ ID NO: 17. In some embodiments, the first HPIV-1 oligomer comprises the sequence of SEQ ID NO: 17 with up to two mismatches. In some embodiments, the first HPIV-1 oligomer comprises the sequence of SEQ ID NO: 17.

In some embodiments, the second HPIV-1 amplification oligomer competes for hybridization to an HPIV-1 nucleic acid under stringent conditions with an oligomer having a sequence consisting of SEQ ID NO: 22. In some embodiments, the second HPIV-1 oligomer comprises the sequence of SEQ ID NO: 22 with up to two mismatches. In some embodiments, the second HPIV-1 oligomer comprises the sequence of SEQ ID NO: 22.

In some embodiments, the composition or kit further comprises a third HPIV-1 oligomer configured to hybridize to the HPIV-1 amplicon, and the third oligomer comprises a detectable label.

In some embodiments, the third HPIV-1 oligomer competes for hybridization to an HPIV-3 nucleic acid under stringent conditions with an oligomer having a sequence consisting of SEQ ID NO: 5, 7, 8, 9, 12, 13, 14, 15, 16, 18, 19, 20, 21, 23, or 125. In some embodiments, the 75 or 76, wherein the third HPIV-1 oligomer comprises the sequence of SEQ ID NO: 5, 7, 8, 9, 12, 13, 14, 15, 16, 18, 19, 20, 21, 23, or 125 with up to two mismatches. In some embodiments, the third HPIV-1 oligomer comprises the sequence of SEQ ID NO: 5, 7, 21, 23, or 125. In some embodiments, the third HPIV-1 oligomer comprises the sequence of SEQ ID NO: 8, 9, 20, or 125. In some embodiments, the third HPIV-1 oligomer comprises the sequence of SEQ ID NO: 12, 13, 14, or 15. In some embodiments, the third HPIV-1 oligomer comprises the sequence of SEQ ID NO: 16, 18, or 19.

In some embodiments, the third HPIV-1 oligomer competes for hybridization to an HPIV-3 nucleic acid under stringent conditions with an oligomer having a sequence consisting of SEQ ID NO: 10. In some embodiments, the third HPIV-1 oligomer comprises the sequence of SEQ ID NO: 10 with up to two mismatches. In some embodiments, the third HPIV-1 oligomer comprises the sequence of SEQ ID NO: 10.

In some embodiments, the third HPIV-1 oligomer competes for hybridization to an HPIV-3 nucleic acid under stringent conditions with an oligomer having a sequence consisting of SEQ ID NO: 11. In some embodiments, the third HPIV-1 oligomer comprises the sequence of SEQ ID NO: 11 with up to two mismatches. In some embodiments, the third HPIV-1 oligomer comprises the sequence of SEQ ID NO: 11.

In some embodiments, at least one, at least two, or each of the first, second, and third HPIV-1 oligomers comprise at least one 5-methylcytosine. In some embodiments, at least about half of the C residues in the first, second, and/or third HPIV-1 oligomers are 5-methylated. In some embodiments, substantially all of the C residues in the first, second, and/or third HPIV-1 oligomers are 5-methylated.

In some embodiments, a kit or composition further comprises a first Human Parainfluenza Virus 1 (HPIV-2) amplification oligomer and a second HPIV-2 amplification oligomer, wherein: the first HPIV-2 amplification oligomer and second HPIV-2 amplification oligomer are configured to amplify an HPIV-2 amplicon of at least about 50 nucleotides in length comprising at least one HPIV-2 position located within HPIV-2 positions 1600-1700.

Also provided herein is a composition or kit comprising at least a first HPIV-2 amplification oligomer and a second HPIV-2 amplification oligomer, wherein: the first HPIV-2 amplification oligomer and second HPIV-2 amplification oligomer are configured to amplify an HPIV-2 amplicon of at least about 50 nucleotides in length comprising at least one HPIV-2 position located within HPIV-2 positions 1600-1700.

Also provided herein is a method of detecting HPIV-2 in a sample, comprising: contacting the sample with at least first and second amplification oligomers, thereby forming a composition, performing a nucleic acid amplification reaction in the composition which produces an HPIV-2 amplicon in the presence of an HPIV-2 nucleic acid, and detecting the presence or absence of the at least one amplicon, wherein: the first HPIV-2 amplification oligomer and second HPIV-2 amplification oligomer are configured to amplify an HPIV-2 amplicon of at least about 50 nucleotides in length comprising at least one HPIV-2 position located within HPIV-2 positions 1600-1700.

In some embodiments, the first HPIV-2 amplification oligomer is configured to hybridize to a site comprising HPIV-2 position 1603 and the second HPIV-2 amplification oligomer is configured to hybridize to a site comprising HPIV-2 position 1698.

In some embodiments, the first HPIV-2 amplification oligomer competes for hybridization to an HPIV-2 nucleic acid under stringent conditions with an oligomer having a sequence consisting of SEQ ID NO: 44. In some embodiments, the first HPIV-2 oligomer comprises the sequence of SEQ ID NO: 44 with up to two mismatches. In some embodiments, the first HPIV-2 oligomer comprises the sequence of SEQ ID NO: 44.

In some embodiments, the second HPIV-2 amplification oligomer competes for hybridization to an HPIV-2 nucleic acid under stringent conditions with an oligomer having a sequence consisting of SEQ ID NO: 40. In some embodiments, the second HPIV-2 oligomer comprises the sequence of SEQ ID NO: 40 with up to two mismatches. In some embodiments, the second HPIV-2 oligomer comprises the sequence of SEQ ID NO: 40.

In some embodiments, the composition or kit further comprises a third HPIV-2 oligomer configured to hybridize to the HPIV-2 amplicon, and the third oligomer comprises a detectable label.

In some embodiments, the third HPIV-2 oligomer competes for hybridization to an HPIV-3 nucleic acid under stringent conditions with an oligomer having a sequence consisting of SEQ ID NO: 38, 39, 41, 42, 43, or 45. In some embodiments, the third HPIV-2 oligomer comprises the sequence of SEQ ID NO: 38, 39, 41, 42, 43, or 45 with up to two mismatches. In some embodiments, the third HPIV-2 oligomer comprises the sequence of SEQ ID NO: 45. In some embodiments, the third HPIV-2 oligomer comprises the sequence of SEQ ID NO: 43. In some embodiments, the third HPIV-2 oligomer comprises the sequence of SEQ ID NO: 42. In some embodiments, the third HPIV-2 oligomer comprises the sequence of SEQ ID NO: 41. In some embodiments, the third HPIV-2 oligomer comprises the sequence of SEQ ID NO: 39. In some embodiments, the third HPIV-2 oligomer comprises the sequence of SEQ ID NO: 38.

In some embodiments, at least one, at least two, or each of the first, second, and third HPIV-2 oligomers comprise at least one 5-methylcytosine. In some embodiments, at least about half of the C residues in the first, second, and/or third HPIV-2 oligomers are 5-methylated. In some embodiments, substantially all of the C residues in the first, second, and/or third HPIV-2 oligomers are 5-methylated.

In some embodiments, a composition or kit disclosed herein further comprises a first Human Parainfluenza Virus 1 (HPIV-4) amplification oligomer and a second HPIV-4 amplification oligomer, wherein: the first HPIV-4 amplification oligomer and second HPIV-4 amplification oligomer are configured to amplify an HPIV-4 amplicon of at least about 50 nucleotides in length comprising at least one HPIV-4 position located within HPIV-4 positions 620-740, 2130-2410, 2520-3040, or 10090-11980.

Also provided herein is a composition or kit comprising at least a first HPIV-4 amplification oligomer and a second HPIV-4 amplification oligomer, wherein: the first HPIV-4 amplification oligomer and second HPIV-4 amplification oligomer are configured to amplify an HPIV-4 amplicon of at least about 50 nucleotides in length comprising at least one HPIV-4 position located within HPIV-4 positions 620-740, 2130-2410, 2520-3040, or 10090-11980.

Also provided herein is a method of detecting HPIV-4 in a sample, comprising: contacting the sample with at least first and second amplification oligomers, thereby forming a composition, performing a nucleic acid amplification reaction in the composition which produces an HPIV-4 amplicon in the presence of an HPIV-4 nucleic acid, and detecting the presence or absence of the at least one amplicon, wherein: the first HPIV-4 amplification oligomer and second HPIV-4 amplification oligomer are configured to amplify an HPIV-4 amplicon of at least about 50 nucleotides in length comprising at least one HPIV-4 position located within HPIV-4 positions 620-740, 2130-2410, 2520-3040, or 10090-11980.

In some embodiments, the first HPIV-4 amplification oligomer is configured to hybridize to a site comprising HPIV-4 position 10094, 10205, or 10248, and the second HPIV-4 amplification oligomer is configured to hybridize to a site comprising HPIV-4 position 11685, 11739, or 11981.

In some embodiments, the first HPIV-4 amplification oligomer competes for hybridization to an HPIV-4 nucleic acid under stringent conditions with an oligomer having a sequence consisting of SEQ ID NO: 79, 80, 81, 82, 97, 98, 99, or 100. In some embodiments, the first HPIV-4 oligomer comprises the sequence of SEQ ID NO: 79, 80, 81, 82, 97, 98, 99, or 100 with up to two mismatches. In some embodiments, the first HPIV-4 oligomer comprises the sequence of SEQ ID NO: 79, 80, 81, 82, 97, 98, 99, or 100.

In some embodiments, the second HPIV-4 amplification oligomer competes for hybridization to an HPIV-4 nucleic acid under stringent conditions with an oligomer having a sequence consisting of SEQ ID NO: 54, 63, 64, 113, 114, or 115. In some embodiments, the second HPIV-4 oligomer comprises the sequence of SEQ ID NO: 54, 63, 64, 113, 114, or 115 with up to two mismatches. In some embodiments, the second HPIV-4 oligomer comprises the sequence of SEQ ID NO: 54, 63, 64, 113, 114, or 115.

In some embodiments, the composition or kit further comprises a third HPIV-4 oligomer configured to hybridize to the HPIV-4 amplicon, and the third oligomer comprises a detectable label.

In some embodiments, the third HPIV-4 oligomer competes for hybridization to an HPIV-3 nucleic acid under stringent conditions with an oligomer having a sequence consisting of SEQ ID NO: 53, 55, 58, 60, 62, 65, 67, 68, 76, 83, 84, 85, 86, 92, 94, 101, 102, 103, 104, 105, 106, 107, 108, 109, 110, 111, or 112. In some embodiments, the third HPIV-4 oligomer comprises the sequence of SEQ ID NO: 53, 55, 58, 60, 62, 65, 67, 68, 76, 83, 84, 85, 86, 92, 94, 101, 102, 103, 104, 105, 106, 107, 108, 109, 110, 111, or 112 with up to two mismatches. In some embodiments, the third HPIV-4 oligomer comprises the sequence of SEQ ID NO: 53, 55, 58, 60, 62, 65, 67, 68, 76, 83, 84, 85, 86, 92, 94, 101, 102, 103, 104, 105, 106, 107, 108, 109, 110, 111, or 112.

In some embodiments, the first HPIV-4 amplification oligomer is configured to hybridize to a site comprising HPIV-4 position 625 and the second HPIV-4 amplification oligomer is configured to hybridize to a site comprising HPIV-4 position 738.

In some embodiments, the first HPIV-4 amplification oligomer competes for hybridization to an HPIV-4 nucleic acid under stringent conditions with an oligomer having a sequence consisting of SEQ ID NO: 78. In some embodiments, the first HPIV-4 oligomer comprises the sequence of SEQ ID NO: 78 with up to two mismatches. In some embodiments, the first HPIV-4 oligomer comprises the sequence of SEQ ID NO: 78.

In some embodiments, the second HPIV-4 amplification oligomer competes for hybridization to an HPIV-4 nucleic acid under stringent conditions with an oligomer having a sequence consisting of SEQ ID NO: 56. In some embodiments, the second HPIV-4 oligomer comprises the sequence of SEQ ID NO: 56 with up to two mismatches. In some embodiments, the second HPIV-4 oligomer comprises the sequence of SEQ ID NO: 56.

In some embodiments, the composition or kit further comprises a third HPIV-4 oligomer configured to hybridize to the HPIV-4 amplicon, and the third oligomer comprises a detectable label.

In some embodiments, the third HPIV-4 oligomer competes for hybridization to an HPIV-3 nucleic acid under stringent conditions with an oligomer having a sequence consisting of SEQ ID NO: 71. In some embodiments, the third HPIV-4 oligomer comprises the sequence of SEQ ID NO: 71 with up to two mismatches. In some embodiments, the third HPIV-4 oligomer comprises the sequence of SEQ ID NO: 71.

In some embodiments, the first HPIV-4 amplification oligomer is configured to hybridize to a site comprising HPIV-4 position 2128, 2352, 2386, 2388, 2404, or 2524 and the second HPIV-4 amplification oligomer is configured to hybridize to a site comprising HPIV-4 position 2907, 3006, or 3039. In some embodiments, the first HPIV-4 amplification oligomer competes for hybridization to an HPIV-4 nucleic acid under stringent conditions with an oligomer having a sequence consisting of SEQ ID NO: 72 or 124. In some embodiments, the first HPIV-4 oligomer comprises the sequence of SEQ ID NO: 72 or 124 with up to two mismatches. In some embodiments, the first HPIV-4 oligomer comprises the sequence of SEQ ID NO: 72 or 124.

In some embodiments, the second HPIV-4 amplification oligomer competes for hybridization to an HPIV-4 nucleic acid under stringent conditions with an oligomer having a sequence consisting of SEQ ID NO: 50, 51, 52, 93, 95, or 96. In some embodiments, the second HPIV-4 oligomer comprises the sequence of SEQ ID NO: 50, 51, 52, 93, 95, or 96 with up to two mismatches. In some embodiments, the second HPIV-4 oligomer comprises the sequence of SEQ ID NO: 50, 51, 52, 93, 95, or 96.

In some embodiments, the composition or kit further comprises a third HPIV-4 oligomer configured to hybridize to the HPIV-4 amplicon, and the third oligomer comprises a detectable label.

In some embodiments, the third HPIV-4 oligomer competes for hybridization to an HPIV-3 nucleic acid under stringent conditions with an oligomer having a sequence consisting of SEQ ID NO: 46, 47, 48, 49, 59, 61, 69, 70, 72, 73, 74, 75, 77, 88, 90, 91, 116, 117, 118, 119, 121, 122, or 123. In some embodiments, the third HPIV-4 oligomer comprises the sequence of SEQ ID NO: 46, 47, 48, 49, 59, 61, 69, 70, 72, 73, 74, 75, 77, 88, 90, 91, 116, 117, 118, 119, 121, 122, or 123 with up to two mismatches. In some embodiments, the third HPIV-4 oligomer comprises the sequence of SEQ ID NO: 46, 47, 48, 49, 59, 61, 69, 70, 72, 73, 74, 75, 77, 88, 90, 91, 116, 117, 118, 119, 121, 122, or 123.

In some embodiments, at least one, at least two, or each of the first, second, and third HPIV-4 oligomers comprise at least one 5-methylcytosine. In some embodiments, at least about half of the C residues in the first, second, and/or third HPIV-4 oligomers are 5-methylated. In some embodiments, substantially all of the C residues in the first, second, and/or third HPIV-4 oligomers are 5-methylated.

In some embodiments of a method disclosed herein, the nucleic acid amplification reaction comprises thermal cycling. In some embodiments of a method disclosed herein, the nucleic acid amplification reaction comprises reverse transcription. In some embodiments of a method disclosed herein, the nucleic acid amplification reaction comprises RT-PCR. In some embodiments of a method disclosed herein, at least one detectable label is fluorescent. In some embodiments, at least one oligomer comprising a fluorescent label further comprises a quencher. In some embodiments, at least one oligomer comprising a fluorescent label is a non-extendable oligomer. In some embodiments of a method disclosed herein, the nucleic acid amplification reaction comprises PCR with a polymerase with 5'-to-3' exonuclease activity, and detecting an amplicon using a probe oligomer comprising a fluorophore and a quencher, wherein exonucleolysis of the probe by the polymerase reduces quenching of fluoresence by the quencher.

In some embodiments, at least one, at least two, or at least three oligomers comprise at least one non-Watson Crick (NWC) position. In some embodiments, at least one, two, three, or four of oligomers configured to hybridize to an HPIV-1, HPIV-2, HPIV-3, or HPIV-4 each comprise at least one NWC position.

In some embodiments, at least one, at least two, or at least three oligomers comprise a degenerate position. In some embodiments, at least one, two, three, or four of oligomers configured to hybridize to an HPIV-1, HPIV-2, HPIV-3, or HPIV-4 each comprise at least one degenerate position.

In some embodiments, the first and second amplification oligomers, the first and second HPIV-1 amplification oligomers, the first and second HPIV-2 amplification oligomers, and/or the first and second HPIV-4 amplification oligomers are comprise target-hybridizing regions from about 10-60 bases in length, about 14-50 bases in length, about 14-40 bases in length, about 14-35 bases in length, or about 15-30 bases in length.

In some embodiments, the HPIV-3 amplicon, the HPIV-1 amplicon, the HPIV-2 amplicon, and/or the HPIV-4 amplicon are about 50-1000 nucleotides, about 50-100 nucleotides, about 100-200 nucleotides, about 200-300 nucleotides, about 300-400 nucleotides, about 400-500 nucleotides, about 500-600 nucleotides, about 600-700 nucleotides, about 700-800 nucleotides, about 800-900 nucleotides, about 900-1000 nucleotides, or about 1000-2000 nucleotides in length.

In some embodiments, a composition disclosed herein is aqueous, frozen, or lyophilized.

Also disclosed herein is a use of a composition or kit disclosed herein for detecting or quantifying an HPIV-1, HPIV-2, HPIV-3, and/or HPIV-4 nucleic acid in a sample.

DETAILED DESCRIPTION OF CERTAIN EMBODIMENTS

Definitions

Before describing the present teachings in detail, it is to be understood that the disclosure is not limited to specific compositions or process steps, as such may vary. It should be noted that, as used in this specification and the appended claims, the singular form "a," "an," and "the" include plural references unless the context clearly dictates otherwise. Thus, for example, reference to "an oligomer" includes a plurality of oligomers and the like. The conjunction "or" is to be interpreted in the inclusive sense, i.e., as equivalent to "and/or," unless the inclusive sense would be unreasonable in the context.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect an HPIV nucleic acid sequence present in a sample with specificity that distinguishes the HPIV nucleic acid from other known respiratory pathogens, optionally at a sensitivity that can detect about 1-100 TCID$_{50}$/ml copies of the virus, and, optionally within about 60 minutes and/or within about 40 cycles from the beginning of an amplification reaction when a cycled amplification reaction is used.

A "sample" or "specimen," including "biological" or "clinical" samples, refers to a tissue or material derived from a living or dead human or animal which may contain a parainfluenza virus target nucleic acid, including, for example, nasopharyngeal or throat swabs, nasal or bronchial or broncheoaveolar washes, nasal aspirates, sputum, other respiratory tissue or exudates, biopsy tissue including lymph nodes, or body fluids such as blood or urine. A sample may be treated to physically or mechanically disrupt tissue or cell structure to release intracellular nucleic acids into a solution which may contain enzymes, buffers, salts, detergents and the like, to prepare the sample for analysis.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., 11th ed., 1992), derivatives of purines or pyrimidines (e.g., $N^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42):13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). 5-methylcytosines may be used in conjunction with any of the foregoing backbones/sugars/linkages including RNA or DNA backbones (or mixtures thereof) unless otherwise indicated. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

"Antisense," "negative-sense," "negative-strand" HPIV nucleic acid refers to the sequence of HPIV present in infectious viruses (or a fragment thereof). "Sense," "positive-sense," or "positive-strand" HPIV nucleic acid is the complement of the sequence of HPIV present in infectious viruses (or a fragment thereof). Exemplary portions of HPIV-1, 2, 3, and 4 are provided in the Sequence Table below (for brevity, complete HPIV genomes, which are known in the art, are not included). Positions or nucleotides of HPIV sequences are defined with reference to the following positions of SEQ ID NO: 1-4, respectively. The first nucleotide of SEQ ID NO: 1 is HPIV-1 position 201. The first nucleotide of SEQ ID NO: 2 is HPIV-2 position 1401. The first nucleotide of SEQ ID NO: 3 is HPIV-3 position 1101. The first nucleotide of SEQ ID NO: 4 is HPIV-4 position 501. Unless otherwise indicated, "hybridizing to an HPIV nucleic acid" includes hybridizing to either a sense or antisense strand of HPIV nucleic acid, e.g., the genomic (antisense) strand, the sense transcript, or either strand of a dsDNA HPIV sequence.

"C residues" include methylated and unmethylated cytosines unless the context indicates otherwise.

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. Unless otherwise indicated, reference to an HPIV nucleic acid includes HPIV RNA and DNA equivalents thereof.

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers may be purified from naturally occurring sources, but may be synthesized by using any well known enzymatic or chemical method. Oligomers may be referred to by a functional name (e.g., capture probe, primer or promoter primer) but those skilled in the art will understand that such terms refer to oligomers.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

An "amplification oligonucleotide" or "amplification oligomer" refers to an oligonucleotide that hybridizes to a target nucleic acid, or its complement, and participates in a nucleic acid amplification reaction, e.g., serving as a primer or and promoter-primer. Particular amplification oligomers contain at least about 10 contiguous bases, and optionally at least 11, 12, 13, 14, 15, 16, 17, 18, 19, or 20 contiguous bases, that are complementary to a region of the target nucleic acid sequence or its complementary strand. The contiguous bases may be at least about 80%, at least about 90%, or completely complementary to the target sequence to which the amplification oligomer binds. One skilled in the art will understand that the recited ranges include all whole and rational numbers within the range (e.g., 92% or 98.377%). Particular amplification oligomers are about 10 to about 60 bases long and optionally may include modified nucleotides.

A "primer" refers to an oligomer that hybridizes to a template nucleic acid and has a 3' end that is extended by polymerization. A primer may be optionally modified, e.g., by including a 5' region that is non-complementary to the target sequence. Such modification can include functional additions, such as tags, promoters, or other sequences used or useful for manipulating or amplifying the primer or target oligonucleotide.

Within the context of transcription mediated amplification, a primer modified with a 5' promoter sequence may be referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308), helicase-dependent amplification (e.g., U.S. Pat. No. 7,282,328), and strand-displacement amplification (SDA) (e.g., U.S. Pat. No. 5,422,252). Amplification may be linear or exponential. Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. Helicase-dependent amplification uses a helicase to separate the two strands of a DNA duplex generating single-stranded templates, followed by hybridization of sequence-specific primers hybridize to the templates and extension by DNA polymerase to amplify the target sequence. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al.). Methods that use TMA are described in detail previously (U.S. Pat. Nos. 5,399,491 and 5,554,516).

In cyclic amplification methods that detect amplicons in real-time, the term "Threshold cycle" (Ct) is a measure of the emergence time of a signal associated with amplification of target, and is generally 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such analytical procedures.

As used herein, the term "relative fluorescence unit" ("RFU") is a unit of measurement of fluorescence intensity. RFU varies with the characteristics of the detection means used for the measurement, and can be used as a measurement to compare relative intensities between samples and controls. The analytical sensitivity (limit of detection or LoD) is determined from the median tissue culture infective dose ($TCID_{50}$/ml). The $TCID_{50}$/ml is that amount of a pathogenic agent that will produce pathological change in 50% of cell cultures inoculated.

"Detection probe" or "probe" refers to an oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and a non-target-complementary sequence. Such non-target-complementary sequences can include sequences which will confer a desired secondary or tertiary structure, such as a hairpin structure, which can be used to facilitate detection and/or amplification (e.g., U.S. Pat. Nos. 5,118,801, 5,312,728, 6,835,542, and 6,849,412). Probes of a defined sequence may be produced by techniques known to those of ordinary skill in the art, such as by chemical synthesis, and by in vitro or in vivo expression from recombinant nucleic acid molecules.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11th ed. 1992).)

By "preferentially hybridize" is meant that under stringent hybridization conditions, an amplification or detection probe oligomer can hybridize to its target nucleic acid to form stable oligomer:target hybrid, but not form a sufficient number of stable oligomer:non-target hybrids. Amplification and detection oligomers that preferentially hybridize to a target nucleic acid are useful to amplify and detect target nucleic acids, but not non-targeted organisms, especially phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified influenza viruses as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid (such as an HPIV nucleic acid) and not to nucleic acid derived from a closely related non-target nucleic acid. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from one or more strains of HPIV with the oligomers of the present disclosure correspond to a temperature of about 60° C. when the salt concentration, such as a monovalent salt, e.g., KCl, is in the range of about 0.6-0.9 M. Specific hybridization assay conditions are set forth infra in the Examples section. Other acceptable stringent hybridization conditions could be easily ascertained by those having ordinary skill in the art.

By "competes for hybridization to an HPIV nucleic acid under stringent conditions" with a referenced oligomer is meant that an oligomer substantially reduces the binding of the referenced oligomer to its target HPIV sequence under stringent conditions, the competing oligomer when supplied in excess can reduce binding of the referenced oligomer at a sub-saturating concentration by about 20%, 30%, 40%, 50%, or more, or the Tm of the competing oligomer is higher than or within about 5, 4, 3, 2, or 1° C. of the Tm of the referenced oligomer to the target. Suitable oligonucleotide competition assay conditions and procedures are known in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, e.g., BLACK HOLE QUENCHER™ (or BHQ™) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Particular homogeneous detectable labels include chemiluminescent compounds, including acridinium ester ("A E") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual*, 2nd ed. (Cold Spring Harbor Laboratory Press, Cold Spring Harbor, NY, 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan™ probes, molecular torches, and molecular beacons. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences may contain one or more residues (including abasic positions) that are not complementary so long as the entire sequences in appropriate hybridization conditions to form a stable hybridization complex. Sufficiently complementary sequences may be at least about 80%, at least about 90%, or completely complementary in the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual*, 2nd ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure may be at least 10 bases in length, and may be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated.

A "degenerate" position in an oligomer refers to a position where more than one base pair is present in a population of the oligomer. For example, in SEQ ID NO: 5, the third nucleotide is Y, which represents C or T/U. Oligomers with degenerate positions can be synthesized by providing a mixture of nucleotide precursors corresponding to the desired degenerate combination at the step of the synthesis where incorporation of a degenerate position is desired.

A "non-Watson Crick" (NWC) position in an oligomer refers to a position where the oligomer is configured to hybridize to at least one HPIV target sequence with a non-Watson Crick pairing, such as G-U, G-T, or G-A (either the G or the U/T/A can be the base in the oligomer). In some embodiments, the NWC position is configured to hybridize via a wobble (G-U) or purine-purine (G-A) pair. In some embodiments, the NWC position is configured to hybridize via a G-T pair. In some embodiments, the NWC position is configured to hybridize via a G-U pair. In some embodiments, the NWC position is configured to hybridize via a G-A pair.

Unless defined otherwise, all scientific and technical terms used herein have the same meaning as commonly understood by those skilled in the relevant art. General definitions may be found in technical books relevant to the art of molecular biology, e.g., DICTIONARY OF MICROBIOLOGY AND MOLECULAR BIOLOGY, 2nd ed. (Singleton et al., 1994, John Wiley & Sons, New York, NY) or THE HARPER COLLINS DICTIONARY OF BIOLOGY (Hale & Marham, 1991, Harper Perennial, New York, NY).

Exemplary Compositions, Kits, Methods, and Uses

The present disclosure provides oligomers, compositions, and kits, useful for amplifying, detecting, or quantifying HPIV-1, 2, 3, and/or 4 from a sample.

In some embodiments, oligomers are provided, e.g., in a kit or composition. Oligomers generally comprise a target-hybridizing region, e.g., configured to hybridize specifically to an HPIV nucleic acid. While oligomers of different lengths and base composition may be used for amplifying HPIV nucleic acids, in some embodiments oligomers in this disclosure have target-hybridizing regions from about 10-60 bases in length, about 14-50 bases in length, about 14-40 bases in length, about 14-35 bases in length, or about 15-30 bases in length. In some embodiments, an oligomer comprises a second region of sequence in addition to the target-hybridizing region, such as a promoter, which can be located 5' of the target-hybridizing region. In some embodiments, an oligomer does not comprise a second region of sequence.

In some embodiments, a pair of oligomers is provided wherein one oligomer is configured to hybridize to a sense strand of an HPIV nucleic acid and the other is configured to hybridize to an anti-sense strand of an HPIV nucleic acid. Such oligomers include primer pairs for PCR or other forms of amplification.

In some embodiments, one or more oligomers, such as a primer pair or a primer pair and a third oligomer which is optionally labeled (e.g., for use as a probe), are configured to hybridize to an HPIV hemagglutinin-neuraminidase (HN) gene. In some embodiments, the HN gene is an HPIV-1, 2, or 3 HN gene. In some embodiments, a plurality of oligomers, such as a plurality of primer pairs or a plurality of primer pairs and third oligomers which are optionally labeled (e.g., for use as a probe), are provided which collectively hybridize to the HN gene of HPIV-1 and 2; HPIV-1 and 3; HPIV-2 and 3; or HPIV-1, 2, and 3.

In some embodiments, one or more oligomers, such as a primer pair or a primer pair and a third oligomer which is optionally labeled (e.g., for use as a probe), are configured to hybridize to an HPIV nucleocapsid (NP) gene. In some embodiments, the NP gene is an HPIV-4 NP gene, such as an HPIV-4a or 4b NP gene. In some embodiments, the one or more oligomers are configured to hybridize to either or both of an HPIV-4a or 4b NP gene.

In some embodiments, one or more oligomers comprise a degenerate position. In some embodiments, an HPIV-1 primer, an HPIV-1 primer pair, and/or an HPIV-1 probe comprises a degenerate position. In some embodiments, an HPIV-3 primer, an HPIV-3 primer pair, and/or an HPIV-3 probe comprises a degenerate position. In some embodiments, an HPIV-4 primer, an HPIV-4 primer pair, and/or an HPIV-4 probe comprises a degenerate position. In some embodiments, the degenerate position is Y, R, S, W, K, or M. Exemplary oligomers with degenerate positions (e.g., Y, R, S, W, K, or M) are listed in the Sequence Table below.

In some embodiments, one or more oligomers comprise a non-Watson Crick (NWC) position. In some embodiments, an HPIV-1 primer, an HPIV-1 primer pair, and/or an HPIV-1 probe comprises a NWC position. In some embodiments, an HPIV-2 primer, an HPIV-2 primer pair, and/or an HPIV-2 probe comprises a degenerate position. In some embodiments, an HPIV-2 primer, an HPIV-2 primer pair, and/or an HPIV-2 probe comprises a NWC position. In some embodiments, an HPIV-3 primer, an HPIV-3 primer pair, and/or an HPIV-3 probe comprises a NWC position. In some embodiments, an HPIV-4 primer, an HPIV-4 primer pair, and/or an HPIV-4 probe comprises a NWC position.

Exemplary NWC positions include U residues in various exemplary oligomers in the Sequence Table. Additional exemplary NWC positions include the G at position 11 of SEQ ID NO: 38; and the G at position 8 of SEQ ID NO: 78.

In some embodiments, one or more oligomers in a set, kit, composition, or reaction mixture comprise a methylated cytosine (e.g., 5-methylcytosine). In some embodiments, at least about half of the cytosines in an oligomer are methylated. In some embodiments, all or substantially all (e.g., all but one or two) of the cytosines in an oligomer are methylated. In some embodiments, a cytosine at the 3' end or within 2, 3, 4, or 5 bases of the 3' end is unmethylated.

Exemplary primer pairs and optional third oligomers are set forth in the following table.

TABLE A

Exemplary oligomer sets. Oligomers are referred to by their SEQ ID NO (see the Sequence Table below).

| Oligomer 1 (e.g., forward primer) | Oligomer 2 (e.g., reverse primer) | Oligomer 3 (optionally labeled, e.g., probe) |
|---|---|---|
| HPIV-1 | | |
| 6 | 24 | 10 or 11 |
| 17 | 22 | 5, 7, 8, 9, 12, 13, 14, 15, 16, 18, 19, 20, 21, 23, or 125 |
| HPIV-2 | | |
| 44 | 40 | 38, 39, 41, 42, 43, or 45 |
| HPIV-3 | | |
| 25 | 36 | 26, 27, 28, 29, or 30 |
| 28 | 37 | 31, 32, 33, 34, or 35 |
| HPIV-4 | | |
| 72 | 50, 51, 52, 93, 95, or 96 | 46, 47, 48, 49, 59, 61, 69, 70, 72, 73, 74, 75, 77, 88, 90, 91, 116, 117, 118, 119, 121, 122, or 123 |
| 78 | 56 | 71 |
| 79, 80, 81, 82, 97, 98, 99, or 100 | 54 | 53, 55, 58, 60, 62, 65, 67, 68, 76, 83, 84, 85, 86, 92, 94, 101, 102, 103, 104, 105, 106, 107, 108, 109, 110, 111, or 112 |
| 79, 80, 81, 82, 97, 98, 99, or 100 | 63 | 53, 55, 58, 60, 62, 65, 67, 68, 76, 83, 84, 85, 86, 92, 94, 101, 102, 103, 104, 105, 106, 107, 108, 109, 110, 111, or 112 |
| 79, 80, 81, 82, 97, 98, 99, or 100 | 64 | 53, 55, 58, 60, 62, 65, 67, 68, 76, 83, 84, 85, 86, 92, 94, 101, 102, 103, 104, 105, 106, 107, 108, 109, 110, 111, or 112 |
| 79, 80, 81, 82, 97, 98, 99, or 100 | 113 | 53, 55, 58, 60, 62, 65, 67, 68, 76, 83, 84, 85, 86, 92, 94, 101, 102, 103, 104, 105, 106, 107, 108, 109, 110, 111, or 112 |
| 79, 80, 81, 82, 97, 98, 99, or 100 | 114 | 53, 55, 58, 60, 62, 65, 67, 68, 76, 83, 84, 85, 86, 92, 94, 101, 102, 103, 104, 105, 106, 107, 108, 109, 110, 111, or 112 |
| 79, 80, 81, 82, 97, 98, 99, or 100 | 115 | 53, 55, 58, 60, 62, 65, 67, 68, 76, 83, 84, 85, 86, 92, 94, 101, 102, 103, 104, 105, 106, 107, 108, 109, 110, 111, or 112 |
| 124 | 50, 51, 52, 93, 95, or 96 | 46, 47, 48, 49, 59, 61, 69, 70, 72, 73, 74, 75, 77, 88, 90, 91, 116, 117, 118, 119, 121, 122, or 123 |

In some embodiments, an oligomer is provided that comprises a label. Such an oligomer can be used as a probe. In some embodiments, the labeled oligomer has a sequence corresponding to a SEQ ID NO listed in the Oligomer 3 column of Table A. In some embodiments, the label is a non-nucleotide label. Suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744). A label, such as a fluorescent or chemiluminescent label, can be attached to the probe by a non-nucleotide linker (see. e.g., U.S. Pat. Nos. 5,585,481; 5,656,744; and 5,639,604).

In some embodiments, a probe (e.g., comprising a fluorescent label) further comprises a second label that interacts with the first label. For example, the second label can be a quencher. Such probes can be used, e.g., in TaqMan™ assays, where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label.

In some applications, one or more probes exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see. e.g., U.S. Pat. Nos. 6,849,412; 6,835,542; 6,534,274; and 6,361,945) and a "molecular beacon" (see. e.g., U.S. Pat. Nos. 5,118,801 and 5,312,728). Molecular torches include distinct regions of self-complementarity (coined "the target binding domain" and "the target closing domain") which are connected by a joining region (e.g., a —(CH$_2$CH$_2$O)$_3$— linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

Examples of interacting donor/acceptor label pairs that may be used in connection with the disclosure, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

In some embodiments, a labeled oligomer (e.g., probe) is non-extendable. For example, the labeled oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

Also provided by the disclosure is a reaction mixture for determining the presence or absence of an HPIV target nucleic acid or quantifying the amount thereof in a sample. A reaction mixture in accordance with the present disclosure comprises at least one or more of the following: an oligomer combination as described herein for amplification of an HPIV target nucleic acid; and a detection probe oligomer as described herein for determining the presence or absence of an HPIV amplification product. The reaction mixture may further include a number of optional components such as, for example, capture probes, e.g., poly-(k) capture probes as described in US 2013/0209992, which is incorporated herein by reference. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, and dTTP; and/or ATP, CTP, GTP and UTP), and/or enzymes (e.g., a thermostable DNA polymerase, or reverse transcriptase and/or RNA polymerase), and will typically include test sample components, in which an HPIV target nucleic acid may or may not be present. A reaction mixture may include amplification oligomers for only one target region of an HPIV genome, or it may include amplification oligomers for multiple HPIV target regions of the same or different type or subtypes, e.g., one, two, three, or four of HPIV-1, HPIV-2, HPIV-3, and HPIV-4. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

In some embodiments, the reaction mixture comprises KCl. In some embodiments, the KCl concentration is about 50 mM. In some embodiments, the KCl concentration is greater than about 50 mM, e.g., about 60-150 mM, about 75-125 mM, about 80-120 mM, about 85-115 mM, or about 90-110 mM. In some embodiments, the KCl concentration is 55-65, 65-75, 75-85, 85-95, 95-105, 105-115, 115-125, 125-135, or 135-145, wherein each of the foregoing is in mM and is optionally modified by "about". In some embodiments, a composition according to the disclosure comprises KCl, e.g., at any of the foregoing concentrations. In some embodiments, a method according to the disclosure comprises performing an amplification reaction in the presence of KCl, e.g., at any of the foregoing concentrations.

Also provided by the subject disclosure are kits for practicing the methods as described herein. A kit in accordance with the present disclosure comprises at least one or more of the following: an amplification oligomer combination as described herein for amplification of an HPIV target nucleic acid; and at least one detection probe oligomer as described herein for determining the presence or absence of an HPIV amplification product. In some embodiments, any oligomer combination described herein is present in the kit. The kits may further include a number of optional components such as, for example, capture probes, e.g., poly-(k) capture probes as described in US 2013/0209992. Other reagents that may be present in the kits include reagents suitable for performing in vitro amplification such as, e.g., buffers, salt solutions, appropriate nucleotide triphosphates (e.g., dATP, dCTP, dGTP, dTTP; and/or ATP, CTP, GTP and UTP), and/or enzymes (e.g., a thermostable DNA polymerase, or a reverse transcriptase and/or RNA polymerase). Oligomers as described herein may be packaged in a variety of different embodiments, and those skilled in the art will appreciate that the disclosure embraces many different kit configurations. For example, a kit may include amplification oligomers for only one target region of an HPIV genome, or it may include amplification oligomers for multiple HPIV target regions of the same or different type or subtypes, e.g., one, two, three, or four of HPIV-1, HPIV-2, HPIV-3, and HPIV-4. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

Any method disclosed herein is also to be understood as a disclosure of corresponding uses of materials involved in the method directed to the purpose of the method. Any of the oligomers comprising HPIV sequence and any combinations (e.g., kits and compositions) comprising such an oligomer are to be understood as also disclosed for use in detecting or quantifying HPIV, and for use in the preparation of a composition for detecting or quantifying HPIV.

Broadly speaking, methods can comprise one or more of the following components: target capture, in which HPIV nucleic acid (e.g., from a sample, such as a clinical sample) is annealed to a capture oligomer; isolation, e.g., washing, to remove material not associated with a capture oligomer; amplification; and amplicon detection, e.g., amplicon quantification, which may be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above, e.g., washing and amplification, or amplification and detection.

In some embodiments, amplification comprises contacting the sample with at least two oligomers for amplifying an HPIV nucleic acid target region corresponding to an HPIV target nucleic acid, where the oligomers include at least two amplification oligomers as described above (e.g., one or more oriented in the sense direction and one or more oriented in the antisense direction for exponential amplification); (2) performing an in vitro nucleic acid amplification reaction, where any HPIV target nucleic acid present in the sample is used as a template for generating an amplification product; and (3) detecting the presence or absence of the amplification product, thereby determining the presence or absence of HPIV in the sample, or quantifying the amount of HPIV nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the HPIV target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HPIV nucleic acid and other sample components.

Target capture typically occurs in a solution phase mixture that contains one or more capture probe oligomers that hybridize to the HPIV target sequence under hybridizing conditions. For embodiments comprising a capture probe tail, the HPIV-target:capture-probe complex is captured by adjusting the hybridization conditions so that the capture probe tail hybridizes to the immobilized probe. Certain embodiments use a particulate solid support, such as paramagnetic beads.

Isolation can follow capture, wherein the complex on the solid support is separated from other sample components. Isolation can be accomplished by any appropriate technique, e.g., washing a support associated with the HPIV-target-sequence one or more times (e.g., 2 or 3 times) to remove other sample components and/or unbound oligomer. In embodiments using a particulate solid support, such as paramagnetic beads, particles associated with the HPIV-target may be suspended in a washing solution and retrieved from the washing solution, In some embodiments by using magnetic attraction. To limit the number of handling steps, the HPIV target nucleic acid may be amplified by simply mixing the HPIV target sequence in the complex on the support with amplification oligomers and proceeding with amplification steps.

Exponentially amplifying an HPIV target sequence utilizes an in vitro amplification reaction using at least two amplification oligomers that flank a target region to be amplified. In some embodiments, at least first and second oligomers as described above are provided. In some embodiments, a plurality of pairs of oligomers is provided, wherein the plurality comprises oligomer pairs configured to hybridize to at least two, three, of four of an HPIV-1, HPIV-2, HPIV-3, or HPIV-4 nucleic acid. The amplification reaction can be cycled or isothermal. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence, such as, e.g., by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the HPIV genomic RNA, and a probe will bind directly or indirectly to a sequence contained in the amplified product to indicate the presence of HPIV nucleic acid in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes are described, e.g., in U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1).

EXAMPLES

The following examples are provided to illustrate certain disclosed embodiments and are not to be construed as limiting the scope of this disclosure in any way.

General Reagents and Methods. Unless otherwise indicated, amplifications were performed using an ABI 7500 FAST® instrument. Viral isolates used as amplification targets or controls were diluted in suitable media, e.g., Micro Test M4 media (Remel Inc. Cat. No. R12500), Micro Test M5 Viral Transport Medium (Remel, Inc. Cat. No. R12515), Micro Test M6 Viral Transport Medium (Remel, Inc. Cat. No. R12530), Micro Test M4RT Viral Transport Medium (Remel, Inc. Cat. No. R12505), or Copan Universal Transport Medium (Copan Diagnostics, Inc., Cat. No. 330C). Nucleic acid was extracted from viral isolates using a non-specific target capture procedure as described in U.S. Patent App. Pub. 2013/0209992.

Results for HPIV-1 through 3 were compared to results obtained in parallel with the Prodesse® ProParaflu+™ Assay, which is discussed in Loeffelholz et al., J. Clin. Microbiol. 49:4083-4088 (2011).

Results for HPIV-4 (including subtypes 4a and 4b) were compared to an FDA cleared HPIV-4 assay (eSensor® Respiratory Virus Panel (GenMark Dx), xTAG™ Respiratory Viral Panel (Luminex), or Biofire FilmArray® Respiratory Panel (BiofireDiagnostics)). The FilmArray® Respiratory Panel is also discussed in Loeffelholz et al., supra. Samples previously characterized as positive for HPIV-4 by one of those three FDA cleared assays were tested with oligomers of the present disclosure. Samples that were discrepant were compared to results generated during development using an alternate buffer and enzyme system on the Cepheid SmartCycler II.

PCR reactions were typically assembled as follows:
19.05 uL Supermix (Promega GoTaq® Supermix)
0.35 uL Roche MMLV Reverse Transcriptase (35 U)
0.6 uL GoTaq MDX Hotstart Taq (3U)
5 uL of nucleic acid (primers, probe, and target in suitable diluent)
=25 uL total reaction volume.

Example 1

Oligomer Design Considerations

For HPIV-1, HPIV-2, and HPIV-3, the hemagglutinin-neuraminidase (HN) gene was targeted. The nucleocapsid protein gene (NP) was targeted for HPIV-4a & 4b detection. It was determined that HPIV-4a and 4b can be detected with the same set of primers and probes.

Due to the lack of sequence conservation among respiratory virus strains and to accommodate known mismatches, degenerate bases and Non-Watson Crick (NWC) bases were considered, e.g., in primers and TaqMan™ probes. NWC base pairing (deoxyguanosine/deoxyuridine or deoxyguanosine/deoxyadenosine) and/or degenerate nucleotides (in which a population of oligomers has individual molecules with one or the other of a pair of bases at degenerate positions) were incorporated in certain positions based on a review of sequence data collected by the inventors. Using Non-Watson Crick bases facilitates the use of a single detection oligonucleotide and thus simplifies manufacturing and quality control, making for a more reproducible process, but can decrease the melting temperature (Tm) of annealed oligomers and assay sensitivity for targets containing the non-Watson Crick base pair(s). In some oligomers, 5-methylcytosine bases were used to increase the stability of the duplex by raising the Tm by about 0.5°-1.3° C. for each 5-methylcytosine incorporated in an oligonucleotide (relative to the corresponding unmethylated oligomer). It was found that cytosine methylation could generally remedy the relatively lower stability of oligomers that used Non-Watson Crick base pairing.

Example 2

Evaluation of Non-Watson Crick Base Pairs

For testing oligomers that use NWC base pairs, reference strains diluted suitable media were extracted as described above and in-vitro transcripts (IVTs) generated in house were diluted in RNase inhibitor/water. Each reference strain or IVT was tested at three anneal temperatures (57° C., 60° C. and 65° C.) with target-specific oligos containing either degenerate bases or Non-Watson Crick bases and 5-methylcytosine. The reference strains or IVTs were selected to match the various mutation combinations observed in the NCBI database at the location of the degenerate and Non-Watson Crick bases. For example, where an A and a G were observed in different strains, a U was used in the NWC oligomer (resulting in either a standard A-U pairing or a G-U wobble NWC pairing); and where a C and an A were observed in different strains, a G was used in the NWC oligomer (resulting in either a standard C-G pairing or a A-G purine-purine NWC pairing). NWC oligomers to be used as probes were designed to hybridize to the plus or minus strand of the target HPIV amplicon as appropriate so that the oligomer would contain a U, G, or A at the NWC position. NWC oligomers to be used as primers were designed to hybridize at sites where the variants or complements thereof predominantly contained either U and A, G and A, C and A, or C and U, or U and G in the strand to which the oligomer hybridizes.

Testing of primers containing Non-Watson Crick base pairing demonstrated that 5-methylcytosine bases increased the Tm and binding stability of the primers to the DNA during PCR such that they produced Ct values similar to those found when using primers with degenerate bases. For example, implementing NWC base pairing and cytosine methylation gave an increase in the range of 0-1.9 Cts for HPIV-2 and 0-3.2 Cts for HPIV-3 compared to the degenerate base oligonucleotides at 57° C. and 60° C. anneal temperatures. At a 65° C. anneal temperature, the NWC oligomers produced Cts that were equal to or earlier than the degenerate base oligonucleotides. In many cases, there was no detection with the degenerate base oligonucleotides at 65° C.

For the evaluation of Non-Watson Crick versus degenerate bases, HPIV-2 and HPIV-3 probes for the Non-Watson Crick oligonucleotides utilized license-free fluorophores and quenchers whereas degenerate base oligonucleotides utilized licensed fluorophores and quenchers obtained from Biosearch. This was due to a limited amount of license-free probes available. An increase in Ct values has been observed with the license-free fluorophores when compared to the licensed fluorophores and quenchers and possibly accounts for the Ct shift observed in the HPIV-2 and HPIV-3 oligonucleotides containing Non-Watson Crick bases. The HPIV-4 degenerate and NWC reactions utilized the same fluorophore/quencher pair and the Ct shift was 1.4-3.1 Cts at 57° C. and only 0.4-1.4 Cts at 60° C.

When license-free fluorophores and quenchers were available for both the Non-Watson Crick/5-methylcytosine probe and the degenerate base probe for HPIV-3, they were run with a 57° C. anneal step to test this possibility. Each HPIV-3 IVT or reference strain was tested in triplicate with both oligonucleotides. The average Ct value for the samples tested with the Non-Watson Crick/5-methylcytosine oligonucleotides were consistently earlier than the Cts for samples tested with the degenerate base oligonucleotides. One IVT was positive in one out of three replicates with the degenerate base oligonucleotides, but was positive in all three replicates with the Non-Watson Crick/5-methylcytosine oligonucleotides. All other samples were positive with both mixes. The total number of unique HPIV-3 samples tested was seven.

The incorporation of the Non-Watson Crick bases with 5-methylcytosine is an acceptable solution that avoids using degenerate bases, which can complicate manufacturing and Quality Control testing relative to oligomers with only non-degenerate positions. It is also possible to use oligomers containing 5-methylcytosine in one, some (e.g., about half) or all positions, without degenerate bases and/or without bases designed to engage in NWC pairing, that can tolerate mismatches in one or a few (e.g., 2 or 3 or 4) bases (due to interstrain sequence variation among viruses) and still function as oligomers, e.g., primers and/or probes.

Example 3

Clinical Specimen Detection and Reactivity

The clinical sensitivity of candidate oligomers was evaluated as described above in the General Reagents and Methods Section using exemplary primer pairs and probes of this disclosure. Seventy-three HPIV-1, 114 HPIV-2, 192 HPIV-3, and 54 HPIV-4 samples were extracted and tested. HPIV-4 samples were also tested with the Cepheid SmartCycler II and reagents obtained from Promega to compare the HPIV-4 clinical specimen detection results and resolve discrepancies.

One HPIV-2 sample was negative upon initial testing with oligomers of this disclosure and 1 HPIV-2 sample was negative with the Prodesse® ProParaflu+™ Assay. Both samples were retested and were positive with the oligomers of this disclosure.

Five HPIV-3 samples were detected by oligomers of this disclosure that were missed by the Prodesse® ProParaflu+™ Assay.

The HPIV-4 samples were previously characterized by an FDA-cleared assay as noted above. During initial testing, 7 samples were negative with oligomers of this disclosure. The HPIV-4 detection was then modified to improve sensitivity and, with a lower threshold and an additional 50 mM KCl (total 100 mM), five out of seven HPIV-4 samples were positive. The hit rate for the HPIV-4 detection of oligomers of this disclosure was 52/54 or 96.3%. The two HPIV-4 negative samples had been previously characterized as HPIV-4 positive during earlier development using the same primers and probes when tested on the Cepheid SmartCycler II with an alternate buffer/enzyme system. The stability of the nucleic acid may have been compromised due to multiple freeze/thaws; therefore the samples were extracted again and tested with the oligomers of this disclosure in duplicate with additional KCl (100 mM total). These replicates were each positive for HPIV-4.

TABLE 1

Hit rate analysis for HPIV clinical samples. PPF+: Prodesse® ProParaflu+™ Assay. IVD Cleared: FDA-cleared assay for HPIV-4 as described above.

HPIV-1:

|  | Oligomers of this disclosure | PPF+ |
|---|---|---|
| # Detected: | 73 | 73 |
| Total: | 73 | 73 |
| Hit Rate: | 100.00% | 100.00% |

HPIV-2:

|  | Oligomers of this disclosure | PPF+ |
|---|---|---|
| # Detected: | 114 | 113 |
| Total: | 114 | 114 |
| Hit Rate: | 100.00% | 99.12% |

HPIV-3:

|  | Oligomers of this disclosure | PPF+ |
|---|---|---|
| # Detected: | 192 | 187 |
| Total: | 192 | 192 |
| Hit Rate: | 100.00% | 97.40% |

HPIV-4:

|  | Oligomers of this disclosure | IVD Cleared |
|---|---|---|
| # Detected: | 54 | 54 |
| Total: | 54 | 54 |
| Hit Rate: | 100.00% | 100.00% |

Due to a limited number of available Human Parainfluenza strains available, one HPIV-1, HPIV-2, HPIV-4a and HPIV-4b, one HPIV-4 (no subtype available) and two HPIV-3 cultured and titered clinical isolates were extracted as described above to test reactivity. Each clinical isolate was tested using the oligomers of this disclosure and the Prodesse® ProParaflu+™ Assay (HPIV-1, HPIV-2 and HPIV-3) at two to three different concentrations in replicates of six on the ABI 7500 FAST®.

The LoD for the additional strains between the oligomers of this disclosure and the Prodesse® ProParaflu+™ Assay was the same for HPIV-1 ($10^1$ $TCID_{50}$/ml) and HPIV-2 ($10^3$ $TCID_{50}$/ml). One of the HPIV-3 strains had the same LoD ($10^1$ $TCID_{50}$/ml) with both assays whereas the other was at least 2 logs better with the oligomers of this disclosure ($10^1$ $TCID_{50}$/ml) compared to the Prodesse® ProParaflu+™ Assay, which detected zero replicates at $10^2$ $TCID_{50}$/ml, the highest concentration tested. LoDs were established for HPIV-4a, HPIV-4b and one HPIV-4 strain that was not designated as subtype a or b. Table 2 contains the reactivity data. Target nucleic acids were isolated from previously characterized stock organisms obtained from TriCore Reference Laboratories (Albuquerque, NM); ZeptoMetrix Corporation (Buffalo, NY); and ATCC (Manassas, VA).

TABLE 2

Reactivity data. PPF+: Prodesse® ProParaflu+™ Assay.

| Strain | LoD & Average Ct PPF+ | LoD & Average Ct Oligomers of this disclosure |
|---|---|---|
| HPIV-1 | $10^1$ $TCID_{50}$/ml, Avg Ct = 37.1 | $10^1$ $TCID_{50}$/ml, Avg Ct = 39.4 |

TABLE 2-continued

Reactivity data. PPF+: Prodesse ® ProParaflu+ ™ Assay.

| Strain | LoD & Average Ct PPF+ | LoD & Average Ct Oligomers of this disclosure |
|---|---|---|
| HPIV-2 | $10^3$ TCID$_{50}$/ml, Avg Ct = 36.8 | $10^3$ TCID$_{50}$/ml, Avg Ct = 37.4 |
| HPIV-3 isolate 1 | Negative at $10^2$ | $10^1$ TCID$_{50}$/ml, Avg Ct = 38.9 |
| HPIV-3 isolate 2 | $10^1$ TCID$_{50}$/ml, Avg Ct = 36.0 | $10^1$ TCID$_{50}$/ml, Avg Ct = 39.0 |
| HPIV-4a | NA | $10^1$ TCID$_{50}$/ml, Avg Ct = 37.3 |
| HPIV-4b | NA | $10^2$ TCID$_{50}$/ml, Avg Ct = 34.6 |
| HPIV-4 (subtype not specified) | NA | $10^2$ TCID$_{50}$/ml, Avg Ct = 35.0 |

The oligomers used for HPIV-3 hybridized to positions encompassing nucleotides 1355, 1380, and 1437 (forward primer, probe, and reverse primer, respectively). The sites to which the oligomers hybridized for HPIV-3 were positions 1349-1371, 1372-1398, and 1426-1448 (forward primer, probe, and reverse primer, respectively); with regard to the numbering of SEQ ID NO: 3, the forward primer, probe, and reverse primer, respectively, for HPIV-3 hybridized to positions 249-271, 272-298, and 326-348. The sequences were SEQ ID NOs: 28, 33, and 37 (forward primer, probe, and reverse primer, respectively). SEQ ID NOs: 34-35 and 31-32 target the same locus as, and may perform similarly to, SEQ ID NO: 33.

Example 4

Analytical Sensitivity

Reference strains were diluted in suitable media, spiked into pooled negative nasopharyngeal swab samples at 4 concentrations and extracted as described above. Each concentration was extracted in 6 replicates and the nucleic acids from the replicates were not combined. From each extraction, 3-4 replicates were used to test the oligomers of this disclosure and the Prodesse® ProParaflu+™ Assay for a total of 20 replicates tested with each assay. Assays were performed on the ABI 7500 FAST®.

The Limit of Detection (LoD) for HPIV-1, HPIV-2 and HPIV-3 was approximately the same between the oligomers of this disclosure and the Prodesse® ProParaflu+™ Assay. The HPIV-1 LoD is $10^1$ TCID$_{50}$/ml, HPIV-2 is $10^0$ TCID$_{50}$/ml and HPIV-3 is $10^1$ TCID$_{50}$/ml. The LoD of HPIV-4a and 4b was established as $10^2$ TCID$_{50}$/ml and $10^0$ TCID$_{50}$/ml, respectively.

TABLE OF SEQUENCES
In the following table, IUPAC nucleotide codes are used to identify degenerate
(mixed) positions (Y = C or T, R = A or G, W = A or T, S = G or C, K = G or T,
M = A or C, etc.) in which individual molecules in a composition or kit may
have any of the nucleotides corresponding to the IUPAC code.

| SEQ ID NO | Description | Sequence |
|---|---|---|
| 1 | Exemplary HPIV-1 sequence, positions 201-1200 | TGAAGACAAACACCATGACAGTATCCTCCGTGAACGAAAGTGCCAAAACAATCAAAGAGACAATCACAGAATTAA TCAGACAAGAAGTGATATCAAGGACTATAAACATACAAAGTTCAGTACAAAGCGGGATCCCAATATTGTTAAACA AGCAAAGCAGAGATCTCACACAATTAATAGAGAAGTCATGCAACAAACAGGAATTGGCTCAGATATGCGAGAACA CTATTGCTATTCACCATGCAGACGGAATAACCCCTCTGGACCCACATGATTTCTGGAGATGTCCCGTAGGAGAAC CCCTATTGAGCAACAACCCTAATATCTCATTATTACCTGGACCAAGTCTACTTTCTGGATCTTCCACAATTTCAG GATGTGTCAGACTACCTTCATTATCAATTGGTGATGCAATATATGCGTATTCATCAAACTTAATCACTCAAGGAT GTGCAGATATAGGGAAGTCATATCAGGTTTTACAATTAGGTTACATATCTTTAAATTCAGATATGTATCCTGATT TAAACCTGGTAATTTCTCATACCTATGACATCAATGACAACAGGAAATCATGTTCTGTAATAGCTGCAGGAACAA GGGGTTACCAGTTATGCTCCTTGCCCACTGTGAATGAGACTACAGATTACTCGAGTGAAGGTATAGAAGACTTAG TATTTGACATATTAGATCTCAAAGGAAAGACCAAATCTCATCGATACAAAAATGAAGATATAACTTTTGACCATC CTTTTTCTGCAATGTATCCAAGTGTAGGAAGTGGGATAAAGATTGAAGATACACTCGTTTTCCTAGGATATGGTG GCTTAACAACTCCGCTTCAAGGCAACACCAAGTGTGTGATAAGCAAATGTCCCAATGTTAATCAGAGTGTTTGCA ATGATGCTCTTAAGATAACTTGGCTAAAGAAAAGACAAGTTGTCAATGTCTTAATTCGTATCAATAATTATTTAT CTGATAGGCCAAAGATTGTTGTCGA |
| 2 | Exemplary HPIV-2 sequence, positions 1401-1900 | ATCATTGAGGCTCAATGGGTACCGTCCTATCAAGTTCCTCGTCCTGGAGTCATGCCATGCAATGCAACAAGTTTT TGCCCTGCTAATTGCATCACAGGGGTGTACGCAGATGTGTGGCCGCTTAATGATCCAGAACTCATGTCACGTAAT GCTCTGAACCCCAACTATCGATTTGCTGGAGCCTTTCTCAAAAATGAGTCCAACCGAACTAATCCCACATTCTAC ACTGCATCGGCTAACTCCCTCTTAAATACTACCGGATTCAACAACACCAATCACAAAGCAGCATATACATCTTCA ACCTGCTTTAAAAACACTGGAACCCAAAAAATTTATTGTTTAATAATAATTGAAATGGGCTCATCTCTTTTAGGG GAGTTCCAAATAATACCATTTTTAAGGGAACTAATGCTTTAATCCTATTGAATGAAGACTCCAGATTCAAGAATA ATTGGAAGGCTCTTTATTTTATGCGATAGTTATACGTTTTGGCTGTATTA |
| 3 | Exemplary HPIV-3 sequence, positions 1101-1600 | TCATAGTCCATGGTTTTCAGATAGAAGGATGGTCAATTCTATAATTGTTGTTGACAAGGGCTTAAACTCAGTTCC AAAATTGAAGGTATGGACGATATCTATGAGACAAAATTACTGGGGGTCAGAAGGAAGATTACTTCTACTAGGTAA CAAGATCTACATATACACAAGATCTACAAGTTGGCACAGCAAGTTACAATTAGGAATAATTGACATTACTGACTA CAGTGACATAAGGATAAAATGGACATGCATAATGTGCTATCAAGACCAGGAAACAATGAATGTCCATGGGGACA TTCATGTCCGGATGGGTGTATAACAGGAGTATATACTGATGCATATCCACTCAATCCCACAGGAAGCATTGTATC ATCTGTCATATTGGACTCACAAAAATCGAGAGTCAACCCAGTCATAACTTACTCAACAGCAACCGAAAGGGTGAA CGAGCTGGCCATTCGGAACAAAACACTCTCAGCTGGGTATACAACAACAA |
| 4 | Exemplary HPIV-4 sequence, positions 501-12100 | TCCAGAGATTTGCCTATCAGCCTTGCCGATAGGACAGTATTTGTATCTAGAGAAGCAGAACATGCAGTGTGTGAC GATATGGATACATACCTGAATAGGATATTCAGTGTATTAATACAGATTTGGATAATGGTGTGCAAATGTATGACA GCCTATGATCAACCCACTGGATCTGAAGAGAGAAGGTTGGCTAAGTACAAGCAGCAGGGCAGGATGTTAGAGAAA TATCAACTGCAAACAGATGCAAGGAAAATTATCCAATTAGTAATAAGAGAGATAGGTTATAAGACAATTTCTT GTACAGGAGATGTTAACAGCTGATAAAGTAGGTGCTTATACTAATAGATATTATGCTATGGTAGGAGATATTGCA AAGTATATAGCCAATGTCGGAATGAGTGCATTCTTTCTTACACTCAAGTTCGGTTTGGGTAACAGGTGGAAACCA CTTGCTCTAGCTGCATTTTCTGGTGAGTTAGTTAAACTAAAGTCTCTTATGTCATTATACAGAAGATTAGGTGAC AGATCAAGATATTTGGCTCTCTTAGAATCTCCTGAATTGATGGAATTTGCTCCAGCCAATTACCCGCTATTATTC AGTTACGCCATGGGAGTTGGAAGTGTCCAGGATCCATTGATCAGAAACTATCAGTTTGGAAGGAACTTCTTAAAC |

TABLE OF SEQUENCES

In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| | | ACCAGCTATTTTCAGTATGGTGTTGAGACTGCAATGAAACACCAGGGTACAGTTGACCCTAAATTGGCCTTAGAG |
| | | CTTGGAATAACTGATGAAGACAGAGTGGATATTATGCAGTCCGTTGAAAAGCACATATCAGGAAAAGCTGGTGAT |
| | | GATATATCACAGCCTGCAGGTGCATTTGCAATGTCTCTAAACAGATCAGCTTTCATTAACAACAACACTTCCCAA |
| | | GACTTCTCAGGGGCAAGACTCTCCAACTACGAGCAAGGATGGTCCGGCACAAATCAAGATGAAACGAGAGATGCC |
| | | TATCCAGAACCTACAATGCATAGACTCCAAAACATTGAATCAACTGACTCAGATCACAATGAACTACTGATGCCG |
| | | GAGCTTGAAAGCGACAGCAACCCCTTCAATCGTCCAAGATTCACAGTCAGAGCACCACTCATCCCAGAAATCTCG |
| | | CACCAGAATCCAAATACCAGAATGAGCAGAGACATCAACACAAGGGACAACATCAGAGCTGACCGTCAAAATACC |
| | | AATGAGGACCGAGGCAGCAACATTCCAGATGACATTCTTGGAGATCTAGACAATTGACACATCAACAACCCAGCC |
| | | ATAGCTAGACAATAATCATAAACCGGGAAAATCTCAAAGATACACAATCGCACACATACAATGAAAGCAATCACT |
| | | TCTGTTCCACATCACAACCCAGAAATCCTGCCAAACGCAACATCACGACCAATCAACTGATGATACACAGTAGAA |
| | | TACAAGAACACAACTGCATTGATTTAAGAAAAAACTAAGATAGGCCTGAACGGTTGCATTCAGGATTCTCAATCG |
| | | TTCAGGCCAATACAATTATCAGCTTCAAACGAAAACAACAAGATGAGCTTTGAAATAAGCATGGAGGAGATTGAC |
| | | GAGCTCATTGAAACTGGCAATCTCAACATAGATTATGCACTTAAAGAATTAGGTGCAACCAGTCAACTCCCGCCA |
| | | AATAATCTCCGTCTCAGACCAGCAAACAGAAGAAACCAACGATGAGACAAGAACCTCAAAAAACTTGGCATCA |
| | | GGAGAGGCACCAGCCCACGCCTCTTCACCACTGCGGTCACACAATGAAGAGAGTGAATCAGGGAAACAGAGCCCA |
| | | GACGGTTTCTCCATGATATCCAACAGACCCCAAACAGGTACACTGCTCATGGGATCAGACACACAATCTCCAAGT |
| | | CCATCAAAGACCTATCAAGGACTCATTCTTGATGCAAAGAAGAGAGCGCTAAATGAACCAAGGAGGAATCAAAAA |
| | | ACAACAAATGAACATGGAAACACAAATGACACCAGGATATTTAAGAGGGGGGAATATAGCCACCAAGAAAGAGGC |
| | | TTGGGTTACACAGGATCAGAGATCAAAAACGCAATCTTCATTCCAAGACATCGAAGGGAATACTCGATTTCATGG |
| | | GTCAACGGAAGAACCACAATATCAGATGGTGCAATCCATGTTGCGCACCAGTCAAACCAACCGCCTCTGTCGAA |
| | | AAGTGTACATGTGGAAGATGTCCCAAAGTTTGCGAATTGTGCATCAGAGATCCTTGATGCAATCAAAGCATTAGA |
| | | GGTGAGGTTAGACAGGATCGAAGGGAAAGTTGACAAAATTATGCTTACTCAAAATACAATTCAGCAAACAAAAAA |
| | | TGACACTCAGCAAATTAAAGGCTCACTTGCAACAATTGAGGGCTAATCACAACAATGAAAATAATGGACCCTGG |
| | | AGTCCCATCAAAAGTAAGTCTTAGAAGCTTAAACAAAGGGCCAGAGCAAGTTCCAATAATCGTCACTGGTACTGG |
| | | CGATGTCTCAAAATTTGTTGATCAAGACAATACAATTACACTTGATCCGTTAGCAAGACCCATTTTGTCTGGAAC |
| | | CAAGCAAACAACTGATGAAAGGAGAGCAGGTGTTCGTATAGATGCACTTAAAATAACAGTATCAGAAATGATTCG |
| | | AGATCTATTTGGAGACTGTGATAAGAGCAGAAAACTTCTTGAATCAATAAACATGGCAACCACAGAGCAAGAAAT |
| | | CAACTTGATCAAAACTAATGCTCTTAGAAGCATCACTTAAACTATGAGATCTATGAATCACGAAGGTCACAGCGA |
| | | CCCAGATTCACTCAATACGCCAAGCGCTCAACCCCACACCCAGAAGGGACAACCGCACCGCATCCCCAAGAATCG |
| | | ACACCAGCTCAGACGACGGCAACACCAATCATCACAAAACAAAACACAGAACATCAGCACTGCATACAAAATCAC |
| | | CCCCCAGCACACACAATCCATCGACCGACAGATTCCCTCCATAACATTACAAAGTATTTAAGAAAAAAACCAGAA |
| | | GTAAGGGGGACCCATCATCCAATCGACTGTGGCCATGGCTCCCACTCAATCCAAAGTCAAAATTCACAATCTAG |
| | | CTGAAGCTCAATGTAAGAAGGTACTGAGAGCCTTCCCAATAGAAGTTGAACAGAACTCAGAAGGGAAGAAACTATTAG |
| | | TGAAACAGATCAGAATAAGAACGCTAGGACATGCGGATCATTCAAATGATTCAATTTGCTTTCTGAATACTTACG |
| | | GGTTTATCAAGGAAGCAGTCAGCCAGACAGAATTCATGAGAGCAGGACAGAGACTAGAAAGCAAAAACACTCTGA |
| | | CTGCTTGCATGTTACCCTTTGGGCCTGGTCCTAACATAGGGTCCCCCAAAAGATGCTAGAATATGCAGAAGACA |
| | | TTAAGATCAATGTAAGAAAGACAGCAGGCTGCAAGGAACAGATTGTGTTTTCTCTAGATAGGACACCTCAAGTGT |
| | | TCAGGGGATTTCAATTTCCCCGGGATAGATATGCATGTGTTCCATCTGACAAATATATAAAATCACCAGGAAAGT |
| | | TAGTCGCAGGACCCAATTATTGTTACATTATCACTTTCCTTTCATTGACATTCGTCCCAGCAGCCAGAAATTCA |
| | | AAGTACCTAGACCCATATTGAATTTTCGATCCACACGAATGAGGGGTATACATCTAGAGATTATCATGAAATTA |
| | | CGTGTTCTGAAAACAGTCCAATCAGAAAGACACTAATAACAGATGATCCCGAAAATGGACCAAAAGCATCCGTGT |
| | | GGATCCACCTCTGTAATCTTTACAAAGGAAGAAATCCTATAAAAGTATATGATGAGGCATATTTTGCAGAGAAAT |
| | | GCAAACAAATGCTGTTAAGCGTAGGTATCAGTGATCTATGGGGGCCCACAATTGCAGTACATGCAAATGGGAAAA |
| | | TCCCCAAATCTGCCAGCCTTTATTTCAACTCAAGAGGATGGGCTTTGCATCCCATAGCTGACGCATCTCCCACAA |
| | | TGGCAAAACAACTATGGTCTATAGGCTGTGAGATCATTGAAGTCAATGCAATATTACAAGGCTCTGATTACAGTG |
| | | CTCTGGTGGATCATCCCGATGTAATATATCGGAAAATCAGAATTGATCCAGCAAAAAGCAGTATGCACACTCTA |
| | | AGTGGAATCCATTCAAGAAGGCAATATCCATGCCTGATCTTGCTGGCATAAATATCTAATCATACAAATTAATCA |
| | | CTGATATAGAGTTAAGGAACATTTTATATTCCTCCCCATTGTATCACCATCACCATCCCGATATATAAAACCACA |
| | | CTACACTATGCACCGTCCAACATCCAGCCAACCACAGGATCACAACACACTACACCAACTCAATCAAGGACATC |
| | | CCTGCAAACATCAAACAACCAAACCATGACTGTAACAGACACAGCACCACCCGACCAAGCCAGACCCTCACCATG |
| | | CACCCAAGTCACCCGACACAACCGCAAACTCTCGACTCTACCATTCGACACACATCCTCGAACAGACCACCCAAA |
| | | AACACCGAACAATTAATCTCCTGGTCACAACGATCATTGTAAATTTTAAGAAAAAATCTAACACACAACTAGAGC |
| | | CAAACACAGGGGGGAAAAACGCATCCGCCGCCACACGCACAGATCCAGAACCCAAGGCAACCAACACCCGTCGG |
| | | ACTCCGCTCCATCTTCAAAGAAATCAACATGGGTGTCAAAGGTCTACCTCTAGTTATGATTGGATTATTAATCTC |
| | | ACCAATTACCAATTTGGATATAACTCATCTAATGAATCTAGGAACGGTACCAACTGCAATTAGATCTCTAGTTTA |
| | | TTACACCTACAGTAAACCATCCTATCTCACCGTAGATTTGATTCCCAATTTGAAGAATCTAGACCCAAAATGCAA |
| | | TTACTCAAGTTTAAATTACTACAATAAAACGGTGTTAAGCTTGATTCAACCAATTGCAGACAATATCAATCACCT |
| | | TACAAAGCCAATCACAAGCTCAGAAATTCAAAGTCGTTCTTTGGGGCAGTTATAGGTACAGTTGCTCTCGGTGT |
| | | AGCTACTGCTGCACAAGTTACAGCAGCCAATCGGTCTTGCAAAAGCTCAGGAAAATGCACGACTTATACTAACTCT |
| | | CAAAAAGCTGCAGAGGAAACAAATGATGCAGTTCGAGATCTCATAGATTCCAACAAAATTGTGGCAAGGATGAT |
| | | ATCAGCAATTCAGAATCAGATAAACACTGTCATTCAACCTGCCATAGACCGGATTGACTGTCAAATCAAGACTT |
| | | ACAAGCTGCTAATATTTTAAATTTGTACCTAACAGAGATCACAACTGTTTTCCACAATCAATTGACCAATCCTGC |
| | | ATTAGAATCATTAGTATTCAGGCTCTCAAAAGTCTTCTAGGATCTACCTTACCAGAAGTGCTGTCTAAGTTAGA |
| | | TCTAAACAATATCTCGGCAGCTTCAGTGATGGCATCTGGCTTAATTAAAGGACAGATAATTGCAGTTGATATACC |
| | | GACTATGACATTAGTGTTGATGGTCCAAATACCAAGTATCTCTCCTCTACGACAAGCAAAATAATAGATCTAAC |
| | | CTCTATAACAATTCACACAAATAATCAGGAAGTACAAGCTGTGGTACCAGATAGAGTTCTTGAGATTGGTTCAGA |
| | | GATATTAGGATTTGACGGTTCAGTGTGCCAAATCACGAAAGATACAATCTTTTGTCCCTACAATGATGCATATAT |
| | | ATTACCCATCCAGCAGAAAAGATGCCTACAAGGTCAAACAAGAGATTGCGTGTTCACCCCGGTTGCTGGCACCTT |
| | | TCCTAGGAGATTTCTCACTACATATGGTACTATAGTAGCCAATTGCAGAAATTTAGTATGTTCTTGTCTACGACC |

-continued

TABLE OF SEQUENCES
In the following table, IUPAC nucleotide codes are used to identify degenerate
(mixed) positions (Y = C or T, R = A or G, W = A or T, S = G or C, K = G or T,
M = A or C, etc.) in which individual molecules in a composition or kit may
have any of the nucleotides corresponding to the IUPAC code.

| SEQ ID NO | Description | Sequence |
|---|---|---|
| | | TCCCCAAATAATCTACCAACCTGATGAGAATCCAGTTACAATCATAGATAAAGACTTATGTACAACATTGACTCT
AGACTCCATAACTATAGAGATCCAGAAATCCATAAATAGTACTTTTCGACGTGAAGTAGTTCTAGAATCTACTCA
GGTTAGATCTTTGACTCCTCTTGATTTATCGACCGATTTAAGTCAATATAATCAATTACTCAAGAGTGCTGAGGA
CCACATCCAACGGTCAAATGATTACTTAAACTCAATCAATCCTAGTATAGTAAATAATAGCGCAATAATAATATT
GATTATACTCTGCATCTTATTAATACTGACAGTCACAATCTGCATAATTTGGCTCAAGTATTTGACCAAAGAAGT
TAGGAATGTAGCAAGAAATCAAAGACTCAATAGAGATGCTGATCTTATTTATAAGATTCCCAGTCAAATTCCATT
GCCCAGATAAATTGCACCAAGAGGCACATTTTGCAAATCTTACCCAGACGCTCCTAGATAAATCGCCTACAAAGA
AAAATAAACTCCCAATTTATCAAAAGAAATCCAAAATCAACGGAGCTACAGCCATCCTGCAATAACACTGCGACC
ACAATGATACTCTTCAAGAAATGAAGGACAAATCCAGAAACAGAAAAAAATAGCCCAAAACAAATTAACAGACAG
AGAAAGGGAGAAGCAAACCCGTCTCAGCAAAACCTCCCATCAACAGCACTCGACCAAGACCGAATTAACAGCACG
AACGCAGAAACCCACTACCACAAAACCACAGAAATTCTCCCATAATCCCCCACCAACATTCACCAACAAATCAGA
AAATCATTCAACCAGGCAACCTCCACATTTCAAGTTTAAGAAAAAAACTATTATAGGGGGGAACGCACTTCTCAG
CTCCAACCACACGAGGCCTTGTCTTGTAAAACAGAATCAATCTCACAAAGTTCAAAACAAAATCTGACTACAAGT
GGAACCTCCACAATTCAAAATTCAACCAACGATCTAACAACAACTCATCAACTAGCAACCATCACTGAACTCAAC
AATCCAGAAGGACGTCACATCAATTCATTCGTGAATCTCCAAAAGAAATAACCCAAGTAAATTTACAATCTACTC
TTTAATTATAAATAAACTAAAGTAAGTCACAAGGATGCAAGATTCACGTGGCAATACTCAAATATTCAGCCAAGC
AAATTCAATGGTAAAAAGAACATGGAGATTACTATTCCGGATTGTAACTTTAATATTACTTATTTCAATATTTGT
GTTGTCACTCATAATTGTACTACAATCAACTCCAGGGAATTTGCAAAGTGATGTCGATATAATCAGAAAAGAGCT
CGATGAACTTATGGAGAACTTTGAAACCACCTCTAAATCACTGCTAAGCGTAGCAAATCAAATTACTTATGATGT
ATCAGTTCTCACCCCCATAAGGCAAGAAGCCACTGAAACAAACATTATTGCGAAAATAAAAGATCATTGCAAAGA
TAGGGTAGTTAAAGGAGAGAGCACCTGCACACTGGGTCCAAGCCTCTACATGATGTTTCCTTTCTGAATGGATT
TAACAAATTCTATTTCACATATAGGGACAATGTACAAATCAGACTTAATCCATTATTGAGATTATCCCAATTTTAT
TCCAACTGCTACAACTCCTCATGGATGCATTCGAATTCCATCATTCTCCCTAAGTCAAACTCATTGGTGTTATAC
TCACAATACGATCTTACGGGGATGTGAAGATACAGCATCTAGCAAACATATGTATCTCTAGGAACCTTACAGAC
CTTAGAAAATGGTGATCCTTATTTCAAGGTCGAGTACAGTCATTATTTAAATGATAGAAAGAATCGAAAAAGTTG
CTCAGTGGTTGCTGTCCTTGACGGATGTTTATTGTATTGTGATCATGACCAAAAATGAAACAGAGAATTTCAA
GGATCCTCAATTGGCAACACAATTACTTACATATATATCATACAATGGTACTATCAAAGAGCGTATAATAAATCC
ACCCGGATCATCTAGAGATTGGGTTCACATCTCACCAGGGGTAGGTTCTGGTATTTTGTATTCAAATTACATCAT
ATTTCCCTTATATGGAGGCCTTATGGAAAATTCAATGATATATAATAATCAATCAGGGAAATATTTTTTCCCTAA
TTCAACCAAGTTGCCATGTAGTAATAAAACCAGTGAAAAAATAACAGGAGCAAAAGACTCATACACAATAACTTA
CTTCTCTAAGAGACTTATACAGAGTGCATTTTTGATTTGTGATTTAAGACAATTTCTTTCTGAAGATTGTGAAAT
TTTAATTCCTAGCAATGATCACATGCTAGTTGGTGCAGAGGGTCGCCTATATAATATTGAAAATAATATATTTA
CTATCAGAGAGGATCCAGCTGGTGGCCCTATCCAAGCCTTTATAGAATCAAATTAAATTCTAATAAGAAATATCC
TAGAATAATTGAGATCAAATTTACAAAAATTGAAATAGCTCCAAGACCTGGCAATAAAGATTGCCCAGGAAATAA
AGCTTGCCCAAAAGAATGCATAACAGGAGTTTACCAAGATATATGGCCACTAAGTTATCCTAATACTGCGTTCCC
CCACAAAAAACGAGCGTACTATACAGGTTTTTATCTCAATAATTCGCTTGCGAGACGTAACCCGACATTTTATAC
TGCTGACAATCTAGATTACCATCAACAGGAAAGATTGGGTAAATTTAATCTTACTGCTGGATATTCCACTACAAC
TTGTTTCAAGCAGACTACCACTGCAAGATTATACTGCCTTTACATACTTGAGGTGGGTGACTCAGCTATTGGTGA
TTTTCAGATTTTTCCCTTTTTACGCTCAATAGATCAGGCTATCACTTAATCAATAGGATTACTCTGTAACACAAG
CTGATTTTATAAGGTGAAATATGCTCATATAAAATGGTCAATGGATAAACAATAATAATAATCATTATAACAAAA
TTAAAAGGACAAACAATTACAAGACACTATGAACTAATCAGGAACAAGCATTAACTAACAACAGCCA
ACATGACCAATGACACTCCATGAAACATCATCCATCAATAACAAAAAGTATAATCTATCAATTAGAACCAAACTT
GATCTATTCTAAGTAATCTACCAAGCGAAAACACACACCAAGAATCACCAGCCATCAAATCTGATTAATCCGACA
CAAAAATCCAAACAACCACCGGAACAGGCCCGGTCCTGATAAACAACCTGCCCGGCCACCAGCCCACTCAAATC
AGGACACAATCAATTTCACCCCAATCATCAGTTTAATCCGCAAGTCAAACAAGTCCTTCCACATGCCCAGAGATT
CAATCGATCTGACACATTGCTATATTTTTTAAGAAAAAAGAAAAATGAGTGGGTGAGACATTCTAGTTCTCATAC
ACAGAATAAACTTCGAACCTTGGATGCAGTATGGATCAAAATTGAAGATTGAAGAACTAGGATGATTCCGCACAC
TAACAGACAAGCAATGAGGAATAAAAAGAATAGACAATTGCCCAAGAGGAATGACACAAAGCATCCAACACTAGG
GGGGAAGAGACCACCTCCAAGATGGCTGATCATACTGATGTCCTATTGCCAGAGGTGCATCTGAGTTCCCCCATT
GTACGTCACAAACTCATTTATTATATACTATTAGGAAATTTACCAAATCAAATAAGTCCTGAAGATCTTGGACCT
TTATCTACAATTAATTGGAGCCAAGTTAGAAGAGAAGAAAGCAAATTATGTTTACGTTTAGTATCTGTAAGGAAT
AATCTTTTAAAACATATACCCTCATTGAGAGAGATAGATCCAACACGTCAGTGTAAAAATTTGTATTGGCCACGA
CCTCTTCAGTTTTTTAAGGATTTGGATTTCAACCAATTTAAAGGGAAAATTGAAAGATGGGAAAAAATTCAACAC
GCTACACAGCTTGTAGTTAATAAGAGAATTATGAATTTTTTAGATTTAATTAGTGATAAATTAATATCAAGGAAA
GACTTATTTACAAGTGCTAGGTGCAGACACGAAGGTCATGATAGAGATTCAAGATTAAGAGAACTAGTTGATATT
GAATCGAACTGGAACAAGAATCATTGGTCAAACACTACAAATCTTTTCTTATTAATAAAATATCAAATGAGACTG
TTAAATTTGTCAAATGAAAAAATCTCAAACTGGTCTTCTTGAGGTCAAGTTGGAAGATAGATCAGGTTTAATTATA
ATTACTCCCGATTAGTGTGTATTTATTTCTATAAAGCAAATGTATTAAGCTATTTCACATTTGAAATGATCCTC
ATGATTTCTGATGTATTTGAAGGAAGACAAAATGTCATAGGATTATGTTCAGTCAGTTATTACTTATCTCCTCTA
AAGGATAGAATTAATGACTTGCTTAATTATGTAGATAATTTAGCACTGATTCTAGGAAATAAGGTTTATTCAATA
ATCGCTAATTTAGAAAGCTTAGTTTATGCTAAATTACAATTGAAGGATCCAGTTTTAGAAGTTAGAGGTCAATTC
CATTGTTTTATACTAGAAGAGATTATGGAGATCTTACATGATGTTTTCTCAGTTGATGAGAGTGCTCAAGTGTGT
TCTATACTGTCATCTTTTCTTAGTGGTCTGTCTCCTGACCTTACTGCAGAATTGTTATGTATTATGAGAATGTGG
GGTCATCCCACTTTAACAGCTGCAGGTGCAGCGGGGAAAGTACGTGAATCTATGTGTGCACCAAAGCTACTAGAC
TTTACAACAATTATGAAACATTATCATTCTTTCACACCATACTTATAAATGGGTACAGAAGAAAGCATGGTGGG
ATCTGGCCAACTGTGACGTTAATTGATGGTACCCCAAATTTTATTGTCAGTCTAAAAAATGATAATGCAGAAATA
ATTTATGAAGTGGCATTGAAATACTGGAAATGGATATCACTGATTGAATTTGAAAAATGTTTTTCAGCCGATCCA
GGTGAGGATTTAAGTATATTCATGAAGGATAAAGCAATAAGTTGTAATAAGAAGGATTGGATGAGTGTATTCAGA
CGAAGTCTCATACATGAGAGATGTGCAAAGAATAATTTAGAATGTCCATCAAATGTAAATAGAAGATTGTTATTA |

-continued

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| | | AATTTCTTAAATGACTCAAATTTCGATCCAAATTTAGAATTAGAGTATGTAACTACCCTCCAGTATCTAACTGAT<br>GATAAATTTTGTGCTTCATACTCTTTGAAAGAAAAGGAGATAAAAGAAACTGGGAGAATATTTGCAAAGCTTACG<br>AAGCAAATGAGATCGTGTCAAGTGATAACAGAATCAATGCTTGCTAATCATGCAGGGAAATTATTCAGAGAAAAC<br>GGTGTAGTTCTTGATCAGCTTAAGTTAACAAAATCACTCCTAACTATGAGCCAAATTGGGATCATTTCAAACAAG<br>GAGCGTAAAGCTACAAAGGACTCTATGACAATCCTAAAAGACATTAAGAAGAATAAAAACATACATAAAGAAAAT<br>GAAAAGAAATATGGTTCAGAGAATTCAACCCCTTTCGGAGACTTTGGGAAAAATTTTGGAATAAATACTCCTGAT<br>GATTCATTAGAAATAGCTGCATGTTTTTAACAACAGATTTACAAAAGTATTGTCTTAATTGGAGATACCAAGCA<br>ATAATACCCTTTGCTAGAACATTAAATCGAATGTACGGATATCCTCATCT |
| 5 | HPIV-1 sense oligomer | CTYACACAATTAATAGAGAAGTCATGCAAC |
| 6 | HPIV-1 sense oligomer | GCAATGTATCCAAGTGTAGGAAG |
| 7 | HPIV-1 sense oligomer | CTUACACAATTAATAGAGAAGTCATGCAAC |
| 8 | HPIV-1 sense oligomer | CAGAGATCTCACACAATTAATAGAGAAGTCATGCAAC |
| 9 | HPIV-1 sense oligomer | CAGAGATCTTACACAATTAATAGAGAAGTCATGCAAC |
| 10 | HPIV-1 sense oligomer | TACGGTGGCTTAACAACTCCGCTCCAA |
| 11 | HPIV-1 sense oligomer | TACGGTGGCTTAACAACTCCGCTCCAA |
| 12 | HPIV-1 sense oligomer | CTYACACAATTAATAGAGAAGTCATGCAAC |
| 13 | HPIV-1 sense oligomer | CTYACACAATTAATAGAGAAGTCATGCAAC |
| 14 | HPIV-1 sense oligomer | CTUACACAATTAATAGAGAAGTCATGCAAC |
| 15 | HPIV-1 sense oligomer | CTUACACAATTAATAGAGAAGTCATGCAAC |
| 16 | HPIV-1 sense oligomer | CTUACACAATTAATAGAGAAGTCATGCAAC |
| 17 | HPIV-1 sense oligomer | TACAAAGCGGGATCCCAATATT |
| 18 | HPIV-1 sense oligomer | AGAGATCTUACACAATTAATAGAGAAGTCATGCAAC |
| 19 | HPIV-1 sense oligomer | AGATCTUACACAATTAATAGAGAAGTCATGCAAC |

-continued

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 20 | HPIV-1 sense oligomer | CAGAGATCTYACACAATTAATAGAGAAGTCATGCAAC |
| 21 | HPIV-1 antisense oligomer | GAAUGUGUUAAUUAUCUCUUCAGUACGUUG |
| 22 | HPIV-1 antisense oligomer | CCTACGGGACATCTCCAGA |
| 23 | HPIV-1 antisense oligomer | GAGUGUGUUAAUUAUCUCUUCAGUACGUUG |
| 24 | HPIV-1 antisense oligomer | GAGCATCATTGCAAACACTCTGA |
| 25 | HPIV-3 sense oligomer | ACAAGATCTACAAGTTGGCA |
| 26 | HPIV-3 sense oligomer | AGCAAGTTACAATTAGGAATAATTGA |
| 27 | HPIV-3 sense oligomer | AGCAAGTTACAATTAGGAATAATTGA |
| 28 | HPIV-3 sense oligomer | CATGGCATAATGTGUTATCAAGA |
| 29 | HPIV-3 sense oligomer | AGCAAGTTACAATTAGGAATAATTGA |
| 30 | HPIV-3 sense oligomer | AGCAAGTTACAATTAGGAATAATTGA |
| 31 | HPIV-3 sense oligomer | CCAGGAAACAAYGAATGTCCATGGGGA |
| 32 | HPIV-3 sense oligomer | CCAGGAAACAAUGAATGTCCATGGGGA |
| 33 | HPIV-3 sense oligomer | CCAGGAAACAATGAATGTCCATGGGGA |
| 34 | HPIV-3 antisense oligomer | GGUCCUUUGUUACUUACAGGUACCCCU |
| 35 | HPIV-3 antisense oligomer | GGUCCUUUGUUGCUUACAGGUACCCCU |
| 36 | HPIV-3 antisense oligomer | CACATTATGCCATGTCCATT |

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 37 | HPIV-3 antisense oligomer | GGATATGCATCAGTATAUACTCC |
| 38 | HPIV-2 antisense oligomer | TGTGATTGGTGTTGTTGAATCCGGTAG |
| 39 | HPIV-2 antisense oligomer | TGTGATTGGTRTTGTTGAATCCGGTAG |
| 40 | HPIV-2 antisense oligomer | AAAGCAGGTTGAAGAUGTATATG |
| 41 | HPIV-2 antisense oligomer | UGUGAUUGGUGUUGUUGAAUCCGGUAG |
| 42 | HPIV-2 antisense oligomer | UGUGAUUGGURUUGUUGAAUCCGGUAG |
| 43 | HPIV-2 sense oligomer | ACACUAACCACAACAACUUAGGCCAUC |
| 44 | HPIV-2 sense oligomer | AAATGAGTCCAACCGAACUAATC |
| 45 | HPIV-2 sense oligomer | ACACUAACCAAAACAACUUAGGCCAUC |
| 46 | HPIV-4 antisense oligomer | AGCATAATTTTGTCAACTTTYCCYTC |
| 47 | HPIV-4 antisense oligomer | CATTYTTTGTTTGCTGAATTRTRTTTTGAG |
| 48 | HPIV-4 antisense oligomer | CTCAATTGTKGMAAGTGARCC |
| 49 | HPIV-4 antisense oligomer | CCATTATTTTCATTGTYGTRATTARGCC |
| 50 | HPIV-4 antisense oligomer | CTTACTTTKGATGGGACTCCRGG |
| 51 | HPIV-4 antisense oligomer | CAAGTGTAATTGTATTGTCTTGATCAAC |
| 52 | HPIV-4 antisense oligomer | GTTCCAGAYAASATGGGTCTTGC |
| 53 | HPIV-4 antisense oligomer | GACYTCAAGAAGRCCAGTTTGAG |

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 54 | HPIV-4 antisense oligomer | CAGCTATTTCYAATGSRTCATCAGGAG |
| 55 | HPIV-4 antisense oligomer | CAGTGCTAAATTRTCTACATAATTRAGYAAG |
| 56 | HPIV-4 antisense oligomer | CTGGCATCTGTTTGCAGTTGA |
| 57 | HPIV-4 antisense oligomer | CTCTCSTCAACTGAGAAAACATCATG |
| 58 | HPIV-4 antisense oligomer | CATAGATTCRCGSACTTTCCCYG |
| 59 | HPIV-4 antisense oligomer | CTCAATTGTKGMAAGTGARCC |
| 60 | HPIV-4 antisense oligomer | CATTCTCATAATRCATAACAAYTCTGCAG |
| 61 | HPIV-4 antisense oligomer | CCATTATTTTCATTGTYGTRATTARGCC |
| 62 | HPIV-4 antisense oligomer | CATAGATTCRCGSACTTTCCCYG |
| 63 | HPIV-4 antisense oligomer | CTTGACAYGATCTCATYTGCTTYG |
| 64 | HPIV-4 antisense oligomer | CCRTTYTCTCTRAATAATTTYCCTGC |
| 65 | HPIV-4 sense oligomer | CATGATGTTTTCTCAGTTGAWGAGAG |
| 66 | HPIV-4 sense oligomer | CARGAAAGAGGCYTGGGTTAC |
| 67 | HPIV-4 sense oligomer | CTGCAGARTTGTTATGYATTATGAGAATG |
| 68 | HPIV-4 sense oligomer | GAAGTRGCAYTRAAATACTGGAAATGG |
| 69 | HPIV-4 sense oligomer | GARGGRAAAGTTGACAAAATTATGCT |
| 70 | HPIV-4 sense oligomer | CTCAAAAYAYAATTCAGCAAACAAARAATG |

TABLE OF SEQUENCES
In the following table, IUPAC nucleotide codes are used to identify degenerate
(mixed) positions (Y = C or T, R = A or G, W = A or T, S = G or C, K = G or T,
M = A or C, etc.) in which individual molecules in a composition or kit may
have any of the nucleotides corresponding to the IUPAC code.

| SEQ ID NO | Description | Sequence |
|---|---|---|
| 71 | HPIV-4 sense oligomer | ATCAACCCACTGGATCTGAAGAGAGAAG |
| 72 | HPIV-4 sense oligomer | GGYTCACTTKCMACAATTGAG |
| 73 | HPIV-4 sense oligomer | GGCYTAATYACRACAATGAAAATAATGG |
| 74 | HPIV-4 sense oligomer | AAAGAATTAGGTGCAACCARTC |
| 75 | HPIV-4 sense oligomer | GCTGCTTATGGGAYCAGACAC |
| 76 | HPIV-4 sense oligomer | CRGGGAAAGTWCGYGAATCTATG |
| 77 | HPIV-4 sense oligomer | GTCCRTCAAAGACYTATCAAGGAC |
| 78 | HPIV-4 sense oligomer | AATACAGGTTTGGATAATGGTGTG |
| 79 | HPIV-4 sense oligomer | CCTGAAGATCTTGGACCYYTATC |
| 80 | HPIV-4 sense oligomer | CCCTCATTGAGRGAGRTAGAYCC |
| 81 | HPIV-4 sense oligomer | GTATTGGCCACGACCTCTTCA |
| 82 | HPIV-4 sense oligomer | TATTGGCCACGACCTCTTCAG |
| 83 | HPIV-4 sense oligomer | CAAGGAAAGAYTTATTTACWAGTGCTAGG |
| 84 | HPIV-4 sense oligomer | GAATCRARCTGGAAYAAGAATCATTGG |
| 85 | HPIV-4 sense oligomer | CTCAAACTGGYCTTCTTGARGTC |
| 86 | HPIV-4 sense oligomer | CTTRCTYAATTATGTAGAYAATTTAGCACTG |
| 87 | HPIV-4 sense oligomer | GGYTCACTTKCMACAATTGAG |

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 88 | HPIV-4 sense oligomer | CCRTCAAAGACYTATCAAGGACTC |
| 89 | HPIV-4 sense oligomer | CAAGGACTCATTCTTGATGCAAARAAG |
| 90 | HPIV-4 antisense oligomer | AGCATAATTTTGTCAACTTTYCCYTC |
| 91 | HPIV-4 antisense oligomer | CATTYTTTGTTTGCTGAATTRTRTTTTGAG |
| 92 | HPIV-4 antisense oligomer | CTCTCSTCAACTGAGAAAACATCATG |
| 93 | HPIV-4 antisense oligomer | CTTACTTTKGATGGGACTCCRGG |
| 94 | HPIV-4 antisense oligomer | CCATTTCCAGTATTTYARTGCYACTTC |
| 95 | HPIV-4 antisense oligomer | CAAGTGTAATTGTATTGTCTTGATCAAC |
| 96 | HPIV-4 antisense oligomer | GTTCCAGAYAASATGGGTCTTGC |
| 97 | HPIV-4 sense oligomer | CCTGAAGATCTTGGACCYYTATC |
| 98 | HPIV-4 sense oligomer | CCCTCATTGAGRGAGRTAGAYCC |
| 99 | HPIV-4 sense oligomer | GTATTGGCCACGACCTCTTCA |
| 100 | HPIV-4 sense oligomer | TATTGGCCACGACCTCTTCAG |
| 101 | HPIV-4 sense oligomer | CAAGGAAAGAYTTATTTACWAGTGCTAGG |
| 102 | HPIV-4 sense oligomer | GAATCRARCTGGAAYAAGAATCATTGG |
| 103 | HPIV-4 sense oligomer | CTCAAACTGGYCTTCTTGARGTC |
| 104 | HPIV-4 sense oligomer | CTTRCTYAATTATGTAGAYAATTTAGCACTG |

-continued

TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 105 | HPIV-4 sense oligomer | CATGATGTTTTCTCAGTTGAWGAGAG |
| 106 | HPIV-4 sense oligomer | CTGCAGARTTGTTATGYATTATGAGAATG |
| 107 | HPIV-4 sense oligomer | CRGGGAAAGTWCGYGAATCTATG |
| 108 | HPIV-4 sense oligomer | GAAGTRGCAYTRAAATACTGGAAATGG |
| 109 | HPIV-4 antisense oligomer | GACYTCAAGAAGRCCAGTTTGAG |
| 110 | HPIV-4 antisense oligomer | CAGTGCTAAATTRTCTACATAATTRAGYAAG |
| 111 | HPIV-4 antisense oligomer | CATTCTCATAATRCATAACAAYTCTGCAG |
| 112 | HPIV-4 antisense oligomer | CCATTTCCAGTATTTYARTGCYACTTC |
| 113 | HPIV-4 antisense oligomer | CTTGACAYGATCTCATYTGCTTYG |
| 114 | HPIV-4 antisense oligomer | CCRTTYTCTCTRAATAATTTYCCTGC |
| 115 | HPIV-4 antisense oligomer | CAGCTATTTCYAATGSRTCATCAGGAG |
| 116 | HPIV-4 sense oligomer | GARGGRAAAGTTGACAAAATTATGCT |
| 117 | HPIV-4 sense oligomer | CTCAAAAYAYAATTCAGCAAACAAARAATG |
| 118 | HPIV-4 sense oligomer | GGCYTAATYACRACAATGAAAATAATGG |
| 119 | HPIV-4 sense oligomer | AAAGAATTAGGTGCAACCARTC |
| 120 | HPIV-4 sense oligomer | GCTGCTTATGGGAYCAGACAC |
| 121 | HPIV-4 sense oligomer | GTCCRTCAAAGACYTAT -continued TABLE OF SEQUENCES
In the following table, IUPAC nucleotide codes are used to identify degenerate (mixed) positions (Y = C or T, R = A or G, W = A or T, S = G or C, K = G or T, M = A or C, etc.) in which individual molecules in a composition or kit may have any of the nucleotides corresponding to the IUPAC code.

| SEQ ID NO | Description | Sequence |
|---|---|---|
| 122 | HPIV-4 sense oligomer | CCRTCAAAGACYTATCAAGGACTC |
| 123 | HPIV-4 sense oligomer | CAAGGACTCATTCTTGATGCAAARAAG |
| 124 | HPIV-4 sense oligomer | CARGAAAGAGGCYTGGGTTAC |
| 125 | HPIV-1 sense oligomer | CAGAGATCTUACACAATTAATAGAGAAGTCATGCAAC |

REFERENCE TO SEQUENCE LISTING SUBMITTED AS A TEXT FILE VIA EFS-WEB

A sequence listing is submitted concurrently with the specification as an ASCII formatted text file via EFS-Web, with a file name of "2018-03-23_01159-0021-00US_Seq-Listing.txt", a creation date of Mar. 21, 2018, and a size of 41.9 KB. The sequence listing filed via EFS-Web is part of the specification and is hereby incorporated by reference in its entirety.

What is claimed is:

1. A composition comprising first, second, third, and fourth amplification oligomers, wherein:
 the first amplification oligomer and second amplification oligomer are configured to produce an HPIV-3 amplicon of at least about 50 nucleotides in length comprising at least one Human Parainfluenza Virus 3 (HPIV-3) position located in the range of positions 1350-1360, wherein the first oligomer comprises a target-hybridizing region consisting of the sequence of SEQ ID NO: 25 and the second oligomer comprises a target-hybridizing region consisting of the sequence of SEQ ID NO: 36;
 the third amplification oligomer and fourth amplification oligomer are configured to produce an HPIV-4 amplicon, wherein the third oligomer comprises a target-hybridizing region consisting of the sequence of SEQ ID NO: 78 and the fourth oligomer comprises a target-hybridizing region consisting of the sequence of SEQ ID NO: 56;
 the composition further comprises a fifth oligomer configured to hybridize to the HPIV-3 amplicon;
 the composition further comprises a sixth oligomer configured to hybridize to the HPIV-4 amplicon, wherein the sixth oligomer is a detection probe; and
 the sixth oligomer comprises a non-nucleotide detectable label.

2. A method of detecting HPIV-3 and HPIV-4 in a sample, comprising:
 contacting the sample with the composition according to claim 1,
 performing a nucleic acid amplification reaction to produce an HPIV-3 amplicon of at least about 50 nucleotides in length in the presence of an HPIV-3 nucleic acid and an HPIV-4 amplicon in the presence of an HPIV-4 nucleic acid, and
 performing a detection reaction to detect the presence of at least one amplicon, if present, selected from the group consisting of the HPIV-3 amplicon and the HPIV-4 amplicon.

3. The composition of claim 1, wherein the fifth oligomer competes for hybridization to an HPIV-3 nucleic acid under stringent conditions with an oligomer having a sequence consisting of the sequence of SEQ ID NO: 26.

4. The composition of claim 1, wherein the fifth oligomer comprises the sequence of SEQ ID NO: 26.

5. The composition of claim 1, wherein the fifth oligomer comprises a target-hybridizing region consisting of the sequence of SEQ ID NO: 26.

6. The composition of claim 1, wherein the fifth oligomer consists of the sequence of SEQ ID NO: 26.

7. The composition of claim 1, wherein the fifth oligomer consists of the sequence of SEQ ID NO: 26 and further comprises a detectable label.

8. The composition of claim 1, wherein all or all but one or two of the C residues in one, two, or three of the first, second, and fifth oligomers are 5-methylated.

9. The composition of claim 1, further comprising a first Human Parainfluenza Virus 1 (HPIV-1) amplification oligomer and a second HPIV-1 amplification oligomer, wherein:
 the first HPIV-1 amplification oligomer and second HPIV-1 amplification oligomer are configured to amplify an HPIV-1 amplicon of at least about 50 nucleotides in length comprising at least one HPIV-1 position located within HPIV-1 positions 330-490 or 960-1100.

10. The composition of claim 1, further comprising a first Human Parainfluenza Virus 2 (HPIV-2) amplification oligomer and a second HPIV-2 amplification oligomer, wherein:
 the first HPIV-2 amplification oligomer and second HPIV-2 amplification oligomer are configured to amplify an HPIV-2 amplicon of at least about 50 nucleotides in length comprising at least one HPIV-2 position located within HPIV-2 positions 1600-1700.

11. The composition of claim 1, wherein the fifth oligomer hybridizes to an HPIV nucleic acid at an antisense version of the site to which an oligomer having a sequence consisting of the sequence of SEQ ID NO: 26, 27, 29, or 30 hybridizes.

12. The composition of claim 1, wherein at least one of the oligomers comprises a non-Watson Crick (NWC) position.

13. The composition of claim 1, wherein at least one of the oligomers comprises at least one 5-methylcytosine.

14. The composition of claim 1, wherein the sixth oligomer competes for hybridization to an HPIV-4 nucleic acid under stringent conditions with an oligomer having a sequence consisting of the sequence of SEQ ID NO: 71.

15. The composition of claim 1, wherein the sixth oligomer comprises a target-hybridizing region consisting of the sequence of SEQ ID NO: 71.

16. The composition of claim 1, wherein the sixth oligomer has a sequence consisting of the sequence of SEQ ID NO: 71.

17. The composition of claim 1, wherein the composition is in a kit.

* * * * *

UNITED STATES PATENT AND TRADEMARK OFFICE
CERTIFICATE OF CORRECTION

PATENT NO. : 12,116,620 B2
APPLICATION NO. : 17/072890
DATED : October 15, 2024
INVENTOR(S) : M. Majlessi et al.

Page 1 of 1

It is certified that error appears in the above-identified patent and that said Letters Patent is hereby corrected as shown below:

On the Title Page

| Column | Line | |
| --- | --- | --- |
| (56) Refs Cited | 22 | change "J Virol" to -- J. Virol. -- |
| (56) Refs Cited | 40 | change "decadeoxyribonucleotides" to -- deoxyribonucleotides -- |
| (56) Refs Cited | 60 | change "submitted" to -- (submitted -- |
| (56) Refs Cited | 47 | change "2014 ." to -- 2014. -- |

In the Specification

| Column | Line | |
| --- | --- | --- |
| 1 | 6 | change "2018," to -- 2018, now U.S. Pat. No. 10,844,425, -- |
| 1 | 7 | change "US" to -- U.S. -- |
| 9 | 29 | change "fluoresence" to -- fluorescence -- |
| 10 | 57 | change "broncheoaveolar" to -- bronchoalveolar -- |
| 12 | 42 | change "or and" to -- or a -- |
| 15 | 55 | change "oligonucleotide(s)," to -- oligonucleotide(s)) -- |
| 16 | 13 | change "("A E")" to -- ("AE") -- |
| 20 | 44-45 | change "IAEDANS/fluororescein," to -- IAEDANS/fluorescein -- |
| 23 | 60 | change "of four" to -- or four -- |
| 24 | 58 | change "e.g.," to -- (e.g., -- |

Signed and Sealed this
Eighth Day of April, 2025

Coke Morgan Stewart
*Acting Director of the United States Patent and Trademark Office*

```
                       SEQUENCE LISTING

<160> NUMBER OF SEQ ID NOS: 125

<210> SEQ ID NO 1
<211> LENGTH: 1000
<212> TYPE: DNA
<213> ORGANISM: Human parainfluenza virus 1

<400> SEQUENCE: 1
tgaagacaaa caccatgaca gtatcctccg tgaacgaaag tgccaaaaca atcaaagaga      60
caatcacaga attaatcaga caagaagtga tatcaaggac tataaacata caaagttcag     120
tacaaagcgg gatcccaata ttgttaaaca agcaaagcag agatctcaca caattaatag     180
agaagtcatg caacaaacag gaattggctc agatatgcga gaacactatt gctattcacc     240
atgcagacgg aataaccct ctggacccac atgatttctg gagatgtccc gtaggagaac      300
ccctattgag caacaaccct aatatctcat tattacctgg accaagtcta ctttctggat     360
cttccacaat ttcaggatgt gtcagactac cttcattatc aattggtgat gcaatatatg     420
cgtattcatc aaacttaatc actcaaggat gtgcagatat agggaagtca tatcaggttt     480
tacaattagg ttacatatct ttaaattcag atatgtatcc tgatttaaac ctggtaattt     540
ctcataccta tgacatcaat gacaacagga atcatgttc tgtaatagct gcaggaacaa     600
ggggttacca gttatgctcc ttgcccactg tgaatgagac tacagattac tcgagtgaag     660
gtatagaaga cttagtattt gacatattag atctcaaagg aaagaccaaa tctcatcgat     720
acaaaaatga agatataact tttgaccatc cttttctgc aatgtatcca agtgtaggaa      780
gtgggataaa gattgaagat acactcgttt tcctaggata tggtggctta acaactccgc     840
ttcaaggcaa caccaagtgt gtgataagca aatgtcccaa tgttaatcag agtgtttgca     900
atgatgctct taagataact tggctaaaga aaagacaagt tgtcaatgtc ttaattcgta     960
```
tcaataatta tttatctgat aggccaaaga ttgttgtcga 1000

<210> SEQ ID NO 2
<211> LENGTH: 500
<212> TYPE: DNA
<213> ORGANISM: Human parainfluenza virus 2

<400> SEQUENCE: 2
atcattgagg ctcaatgggt accgtcctat caagttcctc gtcctggagt catgccatgc 60
aatgcaacaa gtttttgccc tgctaattgc atcacagggg tgtacgcaga tgtgtggccg 120
cttaatgatc cagaactcat gtcacgtaat gctctgaacc ccaactatcg atttgctgga 180
gcctttctca aaaatgagtc caaccgaact aatcccacat tctacactgc atcggctaac 240
tccctcttaa atactaccgg attcaacaac accaatcaca aagcagcata tacatcttca 300
acctgcttta aaaacactgg aacccaaaaa atttattgtt taataataat tgaaatgggc 360
tcatctcttt taggggagtt ccaaataata ccatttttaa gggaactaat gctttaatcc 420
tattgaatga agactccaga ttcaagaata attggaaggc tctttatttt atgcgatagt 480
tatacgtttt ggctgtatta 500

<210> SEQ ID NO 3
<211> LENGTH: 500
<212> TYPE: DNA
<213> ORGANISM: Human parainfluenza virus 3

<400> SEQUENCE: 3
tcatagtcca tggttttcag atagaaggat ggtcaattct ataattgttg ttgacaaggg 60
cttaaactca gttccaaaat tgaaggtatg gacgatatct atgagacaaa attactgggg 120
gtcagaagga agattacttc tactaggtaa caagatctac atatacacaa gatctacaag 180
ttggcacagc aagttacaat taggaataat tgacattact gactacagtg acataaggat 240
aaaatggaca tggcataatg tgctatcaag accaggaaac aatgaatgtc catggggaca 300
ttcatgtccg gatgggtgta taacaggagt atatactgat gcatatccac tcaatcccac 360
aggaagcatt gtatcatctg tcatattgga ctcacaaaaa tcgagagtca acccagtcat 420
aacttactca acagcaaccg aaagggtgaa cgagctggcc attcggaaca aaacactctc 480
agctgggtat acaacaacaa 500

<210> SEQ ID NO 4
<211> LENGTH: 11600
<212> TYPE: DNA
<213> ORGANISM: Human parainfluenza virus 4

<400> SEQUENCE: 4
tccagagatt tgcctatcag ccttgccgat aggacagtat ttgtatctag agaagcagaa 60
catgcagtgt gtgacgatat ggatacatac ctgaatagga tattcagtgt attaatacag 120
atttggataa tggtgtgcaa atgtatgaca gcctatgatc aacccactgg atctgaagag 180
agaaggttgg ctaagtacaa gcagcagggc aggatgttag agaaatatca actgcaaaca 240
gatgcaagga aaattatcca attagtaata agagagagta tggttataag acaatttctt 300
gtacaggaga tgttaacagc tgataaagta ggtgcttata ctaatagata ttatgctatg 360
gtaggagata ttgcaaagta tatagccaat gtcggaatga gtgcattctt tcttacactc 420
aagttcggtt tgggtaacag gtggaaacca cttgctctag ctgcattttc tggtgagtta 480

```
gttaaactaa agtctcttat gtcattatac agaagattag gtgacagatc aagatatttg      540
gctctcttag aatctcctga attgatggaa tttgctccag ccaattaccc gctattattc      600
agttacgcca tgggagttgg aagtgtccag gatccattga tcagaaacta tcagtttgga     660
aggaacttct taaacaccag ctattttcag tatggtgttg agactgcaat gaaacaccag     720
ggtacagttg accctaaatt ggccttagag cttggaataa ctgatgaaga cagagtggat     780
attatgcagt ccgttgaaaa gcacatatca ggaaaagctg gtgatgatat atcacagcct     840
gcaggtgcat ttgcaatgtc tctaaacaga tcagctttca ttaacaacaa cacttcccaa     900
gacttctcag gggcaagact ctccaactac gagcaaggat ggtccggcac aaatcaagat     960
gaaacgagag atgcctatcc agaacctaca atgcatagac tccaaaacat tgaatcaact    1020
gactcagatc acaatgaact actgatgccg gagcttgaaa gcgacagcaa ccccttcaat    1080
cgtccaagat tcacagtcag agcaccactc atcccagaaa tctcgcacca gaatccaaat    1140
accagaatga gcagagacat caacacaagg acaacatca gagctgaccg tcaaaatacc      1200
aatgaggacc gaggcagcaa cattccagat gacattcttg gagatctaga caattgacac    1260
atcaacaacc cagccatagc tagacaataa tcataaaccg ggaaaatctc aaagatacac    1320
aatcgcacac atacaatgaa agcaatcact tctgttccac atcacaaccc agaaatcctg    1380
ccaaacgcaa catcacgacc aatcaactga tgatacacag tagaatacaa gaacacaact    1440
gcattgattt aagaaaaaac taagataggc ctgaacggtt gcattcagga ttctcaatcg    1500
ttcaggccaa tacaattatc agcttcaaac gaaaacaaca agatgagctt gaaataagc     1560 atggaggaga ttgacgagct cattgaaact ggcaatctca acatagatta tgcacttaaa    1620
gaattaggtg caaccagtca actcccgcca aataaatctc cgtctcagac cagcaaaaca    1680
gaagaaacca acgatgagac aagaacctca aaaaacttgg catcaggaga ggcaccagcc    1740
cacgcctctt caccactgcg gtcacacaat gaagagagtg aatcagggaa acagagccca    1800 gacggttttct ccatgatatc caacagaccc caaacaggta cactgctcat gggatcagac    1860
acacaatctc caagtccatc aaagacctat caaggactca ttcttgatgc aaagaagaga    1920
gcgctaaatg aaccaaggag gaatcaaaaa acaacaaatg aacatggaaa cacaaatgac    1980
accaggatat ttaagagggg ggaatatagc caccaagaaa gaggcttggg ttacacagga    2040
tcagagatca aaaacgcaat cttcattcca agacatcgaa gggaatactc gatttcatgg    2100
gtcaacggaa gaaccacaat atcagagtgg tgcaatccat gttgcgcacc agtcaaacca    2160
accgcctctg tcgaaaagtg tacatgtgga agatgtccca agtttgcga attgtgcatc    2220 agagatcctt gatgcaatca aagcattaga ggtgaggtta gacaggatcg aagggaaagt    2280
tgacaaaatt atgcttactc aaaatacaat tcagcaaaca aaaaatgaca ctcagcaaat    2340
taaaggctca cttgcaacaa ttgagggcct aatcacaaca atgaaaataa tggaccctgg    2400
agtcccatca aaagtaagtc ttagaagctt aaacaaaggg ccagagcaag ttccaataat    2460
cgtcactggt actggcgatg tctcaaaatt tgttgatcaa gacaatacaa ttacacttga    2520
tccgttagca agacccattt tgtctggaac caagcaaaca actgatgaaa ggagagcagg    2580
tgttcgtata gatgcactta aaataacagt atcagaaatg attcgagatc tatttggaga    2640
ctgtgataag agcagaaaac ttcttgaatc aataaacatg gcaaccacag agcaagaaat    2700
caacttgatc aaaactaatg ctcttagaag catcacttaa actatgagat ctatgaatca    2760
cgaaggtcac agcgacccag attcactcaa tacgccaagc gctcaacccc acacccagaa    2820
gggacaaccg caccgcatcc ccaagaatcg acaccagctc agacgacggc aacaccaatc    2880
```

```
atcacaaaac aaaacacaga acatcagcac tgcatacaaa atcaccccccc agcacacaca    2940 atccatcgac cgacagattc cctccataac attacaaagt atttaagaaa aaaaccagaa    3000
gtaagggggg acccatcatc caatcgactg tggccatggc tcccactcaa tccaaagtca    3060
aaattcacaa tctagctgaa gctcacgaga aggtactgag agccttccca atagaagttg    3120
aacagaactc agaagggaag aaactattag tgaaacagat cagaataaga acgctaggac    3180
atgcggatca ttcaaatgat tcaatttgct ttctgaatac ttacgggttt atcaaggaag    3240
cagtcagcca gacagaattc atgagagcag acagagact agaaagcaaa acactctga     3300 ctgcttgcat gttacccttt gggcctggtc ctaacatagg gtcccccaa aagatgctag     3360 aatatgcaga agacattaag atcaatgtaa gaaagacagc aggctgcaag gaacagattg    3420
tgttttctct agataggaca cctcaagtgt tcagggggatt tcaatttccc cgggatagat   3480
atgcatgtgt tccatctgac aaatatataa aatcaccagg aaagttagtc gcaggaccca    3540
attattgtta cattatcact ttcctttcat tgacattctg tcccagcagc cagaaattca    3600
aagtacctag acccatattg aattttcgat ccacgcgaat gaggggtata catctagaga    3660
ttatcatgaa aattacgtgt tctgaaaaca gtccaatcag aaagacacta ataacagatg    3720
atcccgaaaa tggaccaaaa gcatccgtgt ggatccacct ctgtaatctt tacaaaggaa    3780
gaaatcctat aaaagtatat gatgaggcat attttgcaga gaatgcaaa caaatgctgt     3840 taagcgtagg tatcagtgat ctatgggggc ccacaattgc agtacatgca aatgggaaaa    3900
tccccaaatc tgccagcctt tatttcaact caagaggatg ggctttgcat cccatagctg    3960
acgcatctcc cacaatggca aaacaactat ggtctatagg ctgtgagatc attgaagtca    4020
atgcaatatt acaaggctct gattacagtg ctctggtgga tcatcccgat gtaatatatc    4080
ggaaaatcag aattgatcca gcaaaaaagc agtatgcaca ctctaagtgg aatccattca    4140
agaaggcaat atccatgcct gatcttgctg gcataaatat ctaatcatac aaattaatca    4200
ctgatataga gttaaggaac attttatatt cctccccatt gtatcaccat caccatcccg    4260
atatataaaa ccacactaca ctatgcaccg tccaacatcc agccaaccac aggatcacaa    4320
ccacactaca ccaactcaat caaggacatc cctgcaaaca tcaaacaacc aaaccatgac    4380
tgtaacagac acagcaccac ccgaccaagc cagaccctca ccatgcaccc aagtcacccg    4440
acacaaccgc aaactctcga ctctaccatt cgacacacat cctcgaacag accacccaaa    4500
aacaccgaac aattaatctc ctggtcacaa cgatcattgt aaattttaag aaaaaatcta    4560
acacacaact agagccaaac acaggggggg aaaaacgcat ccgccgccac acgcacagat    4620
ccagaaccca aggcaaccaa cacccgtcgg actccgctcc atcttcaaag aaatcaacat    4680
gggtgtcaaa ggtctacctc tagttatgat tggattatta atctcaccaa ttaccaattt    4740
ggatataact catctaatga atctaggaac ggtaccaact gcaattagat ctctagttta    4800
ttacacctac agtaaaccat cctatctcac cgtagatttg attcccaatt tgaagaatct    4860
agacccaaaa tgcaattact caagtttaaa ttactacaat aaaacggtgt taagcttgat    4920
tcaaccaatt gcagacaata tcaatcacct tacaaagcca atcacaagct cagaaattca    4980
aagtcgtttc tttggggcag ttataggtac agttgctctc ggtgtagcta ctgctgcaca    5040
agttacagca gcaatcggtc ttgcaaaagc tcaggaaaat gcacgactta tactaactct    5100
caaaaaagct gcagaggaaa caaatgatgc agttcgagat ctcatagatt ccaacaaaat    5160
tgtggcaagg atgatatcag caattcagaa tcagataaac actgtcattc aacctgccat    5220
```

```
agaccggatt gactgtcaaa tcaaagactt acaagctgct aatattttaa atttgtacct    5280
aacagagatc acaactgttt tccacaatca attgaccaat cctgcattag aatcaattag    5340
tattcaggct ctcaaaagtc ttctaggatc taccttacca gaagtgctgt ctaagttaga    5400
tctaaacaat atctcggcag cttcagtgat ggcatctggc ttaattaaag gacagataat    5460
tgcagttgat ataccgacta tgacattagt gttgatggtc caaataccaa gtatctctcc    5520
tctacgacaa gcaaaaataa tagatctaac ctctataaca attcacacaa ataatcagga    5580
agtacaagct gtggtaccag atagagttct tgagattggt tcagagatat taggatttga    5640
cggttcagtg tgccaaatca cgaaagatac aatcttttgt ccctacaatg atgcatatat    5700
attacccatc cagcagaaaa gatgcctaca aggtcaaaca agagattgcg tgttcacccc    5760
ggttgctggc acctttccta ggagatttct cactacatat ggtactatag tagccaattg    5820
cagaaattta gtatgttctt gtctacgacc tccccaaata atctaccaac ctgatgagaa    5880
tccagttaca atcatagata aagacttatg tacaacattg actctagact ccataactat    5940
agagatccag aaatccataa atagtacttt tcgacgtgaa gtagttctag aatctactca    6000
ggttagatct ttgactcctc ttgatttatc gaccgattta agtcaatata atcaattact    6060
caagagtgct gaggaccaca tccaacggtc aaatgattac ttaaactcaa tcaatcctag    6120
tatagtaaat aatagcgcaa taataatatt gattatactc tgcatcttat taatactgac    6180
agtcacaatc tgcataattt ggctcaagta tttgaccaaa gaagttagga atgtagcaag    6240
aaatcaaaga ctcaatagag atgctgatct tatttataag attcccagtc aaattccatt    6300
gcccagataa ttgcaaccaa gaggcacatt ttgcaaatct tacccagacg ctcctagata    6360
aatcgcctac aaagaaaaat aaactcccaa tttatcaaaa gaaatccaaa atcaacggag    6420
ctacagccat cctgcaataa cactgcgacc acaatgatac tcttcaagaa atgaaggaca    6480
aatccagaaa cagaaaaaaa tagcccaaaa caaattaaca gacagagaaa gggagaagca    6540
aacccgtctc agcaaaacct cccatcaaca gcactcgacc aagaccgaat taacagcacg    6600
aacgcagaaa cccactacca caaaaccaca gaaattctcc cataatcccc caccaacatt    6660
caccaacaaa tcagaaaatc attcaaccag gcaacctcca catttcaagt ttaagaaaaa    6720
aactattata gggggggaacg cacttctcag ctccaaccac acgaggcctt gtcttgtaaa    6780
acagaatcaa tctcacaaag ttcaaaacaa aatctgacta caagtggaac ctccacaatt    6840
caaaattcaa ccaacgatct aacaacaact catcaactag caaccatcac tgaactcaac    6900
aatccagaag gacgtcacat caattcattc gtgaatctcc aaaagaaata acccaagtaa    6960
atttacaatc tactctttaa ttataaataa actaaagtaa gtcacaagga tgcaagattc    7020
acgtggcaat actcaaatat tcagccaagc aaattcaatg gtaaaaagaa catggagatt    7080
actattccgg attgtaactt taatattact tatttcaata tttgtgttgt cactcataat    7140
tgtactacaa tcaactccag ggaatttgca aagtgatgtc gatataatca gaaaagagct    7200
cgatgaactt atggagaact ttgaaaccac ctctaaatca ctgctaagcg tagcaaatca    7260
aattacttat gatgtatcag ttctcacccc cataaggcaa aagccactg aaacaaacat    7320
tattgcgaaa ataaaagatc attgcaaaga tagggtagtt aaaggagaga gcacctgcac    7380
actgggtcac aagcctctac atgatgtttc ctttctgaat ggatttaaca aattctattt    7440
cacatatagg gacaatgtac aaatcagact taatccatta ttagattatc ccaatttat    7500
tccaactgct acaactcctc atggatgcat tcgaattcca tcattctccc taagtcaaac    7560
tcattggtgt tatactcaca atacgatctt acggggatgt gaagatacag catctagcaa    7620
```

```
acagtatgta tctctaggaa ccttacagac cttagaaaat ggtgatcctt atttcaaggt   7680
cgagtacagt cattatttaa atgatagaaa gaatcgaaaa agttgctcag tggttgctgt   7740
ccttgacgga tgtttattgt attgtgtgat catgaccaaa aatgaaacag agaatttcaa   7800
ggatcctcaa ttggcaacac aattacttac atatatatca tacaatggta ctatcaaaga   7860
gcgtataata aatccacccg gatcatctag agattgggtt cacatctcac caggggtagg   7920
ttctggtatt ttgtattcaa attacatcat atttcccttta tatggaggcc ttatggaaaa   7980
ttcaatgata tataataatc aatcagggaa atatttttc cctaattcaa ccaagttgcc   8040
atgtagtaat aaaaccagtg aaaaaataac aggagcaaaa gactcataca caataactta   8100
cttctctaag agacttatac agagtgcatt tttgatttgt gatttaagac aatttctttc   8160
tgaagattgt gaaattttaa ttcctagcaa tgatcacatg ctagttggtg cagagggtcg   8220
cctatataat attgaaaata atatattta ctatcagaga ggatccagct ggtggcccta   8280
tccaagcctt tatagaatca aattaaattc taataagaaa tatcctagaa taattgagat   8340
caaatttaca aaaattgaaa tagctccaag acctggcaat aaagattgcc caggaaataa   8400
agcttgccca aaagaatgca taacaggagt ttaccaagat atatggccac taagttatcc   8460
taatactgcg ttcccccaca aaaaacgagc gtactataca ggttttttatc tcaataattc   8520
gcttgcgaga cgtaacccga cattttatac tgctgacaat ctagattacc atcaacagga   8580
aagattgggt aaatttaatc ttactgctgg atattccact acaacttgtt tcaagcagac   8640
taccactgca agattatact gcctttacat acttgaggtg ggtgactcag taattggtga   8700
ttttcagatt tttcccttt tacgctcaat agatcaggct atcacttaat caataggatt   8760
actctgtaac acaagctgat tttataaggt gaaatatgct catataaaat ggtcaatgga   8820
taaacaataa taataatcat tataacaaaa ttaaaaggac aaaacaatta caagaacact   8880
atgaactaat caggaaacaa acatagcatt aactaacaac agccaacatg accaatgaca   8940
ctccatgaaa catcatccat caataacaaa aagtataatc tatcaattag aaccaaactt   9000
gatctattct aagtaatcta ccaagcgaaa acacacacca agaatcacca gccatcaaat   9060
ctgattaatc cgacacaaaa atccaaacaa ccaccggaac aggcccggtc ctgataaaca   9120
acctgcccgg ccaccagccc actcaaaatc aggacacaat caatttcacc ccaatcatca   9180
gtttaatccg caagtcaaac aagtccttcc acatgcccag agattcaatc gatctgacac   9240
attgctatat ttttaagaa aaagaaaaa tgagtgggtg agacattcta gttctcatac   9300
acagaataaa cttcgaacct tggatgcagt atggatcaaa attgaagatt gaagaactag   9360
gatgattccg cacactaaca gacaagcaat gaggaataaa aagaatagac aattgcccaa   9420
gaggaatgac acaaagcatc caacactagg ggggaagaga ccacctccaa gatggctgat   9480
catactgatg tcctattgcc agaggtgcat ctgagttccc ccattgtacg tcacaaactc   9540
atttattata tactattagg aaatttacca aatcaaataa gtcctgaaga tcttggacct   9600
ttatctacaa ttaattggag ccaagttaga agagaagaaa gcaaattatg tttacgttta   9660
gtatctgtaa ggaataatct tttaaaacat atacccctcat tgagagagat agatccaaca   9720
cgtcagtgta aaaatttgta ttggccacga cctcttcagt tttttaagga tttggatttc   9780
aaccaattta aagggaaaat tgaaagatgg gaaaaaattc aacacgctac acagcttgta   9840
gttaataaga gaattatgaa ttttttagat ttaattagtg ataaattaat atcaaggaaa   9900
gacttatttta caagtgctag gtgcagacac gaaggtcatg atagagattc aagattaaga   9960
```

```
gaactagttg atattgaatc gaactggaac aagaatcatt ggtcaaacac tacaaatctt    10020
ttcttattaa taaaatatca aatgagactg ttaatttgtc aaatgaaaaa atctcaaact    10080
ggtcttcttg aggtcaagtt ggaagataga tcaggtttaa ttataattac tcccgaatta    10140
gtgtgtattt atttctataa agcaaatgta ttaagctatt tcacatttga aatgatcctc    10200
atgatttctg atgtatttga aggaagacaa aatgtcatag gattatgttc agtcagttat    10260
tacttatctc ctctaaagga tagaattaat gacttgctta attatgtaga taatttagca    10320
ctgattctag gaaataaggt ttattcaata atcgctaatt tagaaagctt agtttatgct    10380
aaattacaat tgaaggatcc agttttagaa gttagaggtc aattccattg tttttatacta   10440 gaagagatta tggagatctt acatgatgtt ttctcagttg atgagagtgc tcaagtgtgt    10500
tctatactgt catcttttct tagtggtctg tctcctgacc ttactgcaga attgttatgt    10560
attatgagaa tgtggggtca tcccactta  acagctgcag gtgcagcggg gaaagtacgt    10620
gaatctatgt gtgcaccaaa gctactagac tttacaacaa ttatgaaaac attatcattc    10680
tttcacacca tacttataaa tgggtacaga agaaagcatg gtgggatctg gccaactgtg    10740
acgttaattg atggtacccc aaattttatt gtcagtctaa aaaatgataa tgcagaaata    10800
atttatgaag tggcattgaa atactggaaa tggatatcac tgattgaatt tgaaaaatgt    10860
ttttcagccg atccaggtga ggatttaagt atattcatga aggataaagc aataagttgt    10920
aataagaagg attggatgag tgtattcaga cgaagtctca tacatgagag atgtgcaaag    10980
aataatttag aatgtccatc aaatgtaaat agaagattgt tattaaattt cttaaatgac    11040
tcaaatttcg atccaaattt agaattagag tatgtaacta ccctccagta tctaactgat    11100
gataaatttt gtgcttcata ctctttgaaa gaaaaggaga taaaagaaac tgggagaata    11160
tttgcaaagc ttacgaagca aatgagatcg tgtcaagtga taacagaatc aatgcttgct    11220
aatcatgcag ggaaattatt cagagaaaac ggtgtagttc ttgatcagct taagttaaca    11280
aaatcactcc taactatgag ccaaattggg atcatttcaa acaaggagcg taaagctaca    11340
aaggactcta tgacaatcct aaaagacatt aagaagaata aaaacataca taaagaaaat    11400
gaaaagaaat atggttcaga gaattcaacc cctttcggag actttgggaa aaattttgga    11460
ataaatactc ctgatgattc attagaaata gctgcatgtt ttttaacaac agatttacaa    11520
aagtattgtc ttaattggag ataccaagca ataatccct  ttgctagaac attaaatcga    11580
atgtacggat atcctcatct                                                11600

<210> SEQ ID NO 5
<211> LENGTH: 30
<212> TYPE: DNA
<213> ORGANISM: Artificial sequence
<220> FEATURE:
<223> OTHER INFORMATION: Synthetic oligomer

<400> SEQUENCE: 5
ctyacacaat taatagagaa gtcatgcaac                                        30

<210> SEQ ID NO 6
<211> LENGTH: 23
<212> TYPE: DNA
<213> ORGANISM: Artificial sequence
<220> FEATURE:
<223> OTHER INFORMATION: Synthetic oligomer

<400> SEQUENCE: 6
gcaatgtatc caagtgtagg aag                                               23
```

<210> SEQ ID NO 7
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(3)
<223> OTHER INFORMATION: n is u

<400> SEQUENCE: 7
ctnacacaat taatagagaa gtcatgcaac                                30

<210> SEQ ID NO 8
<211> LENGTH: 37
<212> TYPE: DNA
<213> ORGANISM: Artificial sequence
<220> FEATURE:
<223> OTHER INFORMATION: Synthetic oligomer

<400> SEQUENCE: 8
cagagatctc acacaattaa tagagaagtc atgcaac                        37

<210> SEQ ID NO 9
<211> LENGTH: 37
<212> TYPE: DNA
<213> ORGANISM: Artificial sequence
<220> FEATURE:
<223> OTHER INFORMATION: Synthetic oligomer

<400> SEQUENCE: 9
cagagatctt acacaattaa tagagaagtc atgcaac                        37

<210> SEQ ID NO 10
<211> LENGTH: 27
<212> TYPE: DNA
<213> ORGANISM: Artificial sequence
<220> FEATURE:
<223> OTHER INFORMATION: Synthetic oligomer

<400> SEQUENCE: 10
tacggtggct taacaactcc gctccaa                                   27

<210> SEQ ID NO 11
<211> LENGTH: 27
<212> TYPE: DNA
<213> ORGANISM: Artificial sequence
<220> FEATURE:
<223> OTHER INFORMATION: Synthetic oligomer

<400> SEQUENCE: 11
tacggtggct taacaactcc gctccaa                                   27

<210> SEQ ID NO 12
<211> LENGTH: 30
<212> TYPE: DNA
<213> ORGANISM: Artificial sequence
<220> FEATURE:
<223> OTHER INFORMATION: Synthetic oligomer

<400> SEQUENCE: 12
ctyacacaat taatagagaa gtcatgcaac                                30

<210> SEQ ID NO 13

```
<211> LENGTH: 30
<212> TYPE: DNA
<213> ORGANISM: Artificial sequence
<220> FEATURE:
<223> OTHER INFORMATION: Synthetic oligomer

<400> SEQUENCE: 13
ctyacacaat taatagagaa gtcatgcaac                              30

<210> SEQ ID NO 14
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(3)
<223> OTHER INFORMATION: n is u

<400> SEQUENCE: 14
ctnacacaat taatagagaa gtcatgcaac                              30

<210> SEQ ID NO 15
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(3)
<223> OTHER INFORMATION: n is u

<400> SEQUENCE: 15
ctnacacaat taatagagaa gtcatgcaac                              30

<210> SEQ ID NO 16
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(3)
<223> OTHER INFORMATION: n is u

<400> SEQUENCE: 16
ctnacacaat taatagagaa gtcatgcaac                              30

<210> SEQ ID NO 17
<211> LENGTH: 22
<212> TYPE: DNA
<213> ORGANISM: Artificial sequence
<220> FEATURE:
<223> OTHER INFORMATION: Synthetic oligomer

<400> SEQUENCE: 17
tacaaagcgg gatcccaata tt                                      22

<210> SEQ ID NO 18
<211> LENGTH: 36
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
```

```
<222> LOCATION: (9)..(9)
<223> OTHER INFORMATION: n is u

<400> SEQUENCE: 18
agagatctna cacaattaat agagaagtca tgcaac                              36

<210> SEQ ID NO 19
<211> LENGTH: 34
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (7)..(7)
<223> OTHER INFORMATION: n is u

<400> SEQUENCE: 19
agatctnaca caattaatag agaagtcatg caac                                34

<210> SEQ ID NO 20
<211> LENGTH: 37
<212> TYPE: DNA
<213> ORGANISM: Artificial sequence
<220> FEATURE:
<223> OTHER INFORMATION: Synthetic oligomer

<400> SEQUENCE: 20
cagagatcty acacaattaa tagagaagtc atgcaac                             37

<210> SEQ ID NO 21
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (4)..(29)
<223> OTHER INFORMATION: n is u

<400> SEQUENCE: 21
gaangngnna annancncnn cagnacgnng                                     30

<210> SEQ ID NO 22
<211> LENGTH: 19
<212> TYPE: DNA
<213> ORGANISM: Artificial sequence
<220> FEATURE:
<223> OTHER INFORMATION: Synthetic oligomer

<400> SEQUENCE: 22
cctacgggac atctccaga                                                 19

<210> SEQ ID NO 23
<211> LENGTH: 30
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (4)..(29)
<223> OTHER INFORMATION: n is u

<400> SEQUENCE: 23
gagngngnna annancncnn cagnacgnng                                     30
```

```
<210> SEQ ID NO 24
<211> LENGTH: 23
<212> TYPE: DNA
<213> ORGANISM: Artificial sequence
<220> FEATURE:
<223> OTHER INFORMATION: Synthetic oligomer

<400> SEQUENCE: 24
gagcatcatt gcaaacactc tga                                               23

<210> SEQ ID NO 25
<211> LENGTH: 20
<212> TYPE: DNA
<213> ORGANISM: Artificial sequence
<220> FEATURE:
<223> OTHER INFORMATION: Synthetic oligomer

<400> SEQUENCE: 25
acaagatcta caagttggca                                                   20

<210> SEQ ID NO 26
<211> LENGTH: 26
<212> TYPE: DNA
<213> ORGANISM: Artificial sequence
<220> FEATURE:
<223> OTHER INFORMATION: Synthetic oligomer

<400> SEQUENCE: 26
agcaagttac aattaggaat aattga                                            26

<210> SEQ ID NO 27
<211> LENGTH: 26
<212> TYPE: DNA
<213> ORGANISM: Artificial sequence
<220> FEATURE:
<223> OTHER INFORMATION: Synthetic oligomer

<400> SEQUENCE: 27
agcaagttac aattaggaat aattga                                            26

<210> SEQ ID NO 28
<211> LENGTH: 23
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (15)..(15)
<223> OTHER INFORMATION: n is u

<400> SEQUENCE: 28
catggcataa tgtgntatca aga                                               23

<210> SEQ ID NO 29
<211> LENGTH: 26
<212> TYPE: DNA
<213> ORGANISM: Artificial sequence
<220> FEATURE:
<223> OTHER INFORMATION: Synthetic oligomer

<400> SEQUENCE: 29
agcaagttac aattaggaat aattga                                            26

<210> SEQ ID NO 30
<211> LENGTH: 26
```

```
<212> TYPE: DNA
<213> ORGANISM: Artificial sequence
<220> FEATURE:
<223> OTHER INFORMATION: Synthetic oligomer

<400> SEQUENCE: 30
agcaagttac aattaggaat aattga                                              26

<210> SEQ ID NO 31
<211> LENGTH: 27
<212> TYPE: DNA
<213> ORGANISM: Artificial sequence
<220> FEATURE:
<223> OTHER INFORMATION: Synthetic oligomer

<400> SEQUENCE: 31
ccaggaaaca aygaatgtcc atggga                                              27

<210> SEQ ID NO 32
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (12)..(12)
<223> OTHER INFORMATION: n is u

<400> SEQUENCE: 32
ccaggaaaca angaatgtcc atggga                                              27

<210> SEQ ID NO 33
<211> LENGTH: 27
<212> TYPE: DNA
<213> ORGANISM: Artificial sequence
<220> FEATURE:
<223> OTHER INFORMATION: Synthetic oligomer

<400> SEQUENCE: 33
ccaggaaaca atgaatgtcc atggga                                              27

<210> SEQ ID NO 34
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(27)
<223> OTHER INFORMATION: n is u

<400> SEQUENCE: 34
ggnccnnngn nacnnacagg nacccn                                              27

<210> SEQ ID NO 35
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (3)..(27)
<223> OTHER INFORMATION: n is u

<400> SEQUENCE: 35
```

```
ggnccnnngn ngcnnacagg naccccn                                27
```

<210> SEQ ID NO 36
<211> LENGTH: 20
<212> TYPE: DNA
<213> ORGANISM: Artificial sequence
<220> FEATURE:
<223> OTHER INFORMATION: Synthetic oligomer

<400> SEQUENCE: 36

```
cacattatgc catgtccatt                                        20
```

<210> SEQ ID NO 37
<211> LENGTH: 23
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (18)..(18)
<223> OTHER INFORMATION: n is u

<400> SEQUENCE: 37

```
ggatatgcat cagtatanac tcc                                    23
```

<210> SEQ ID NO 38
<211> LENGTH: 27
<212> TYPE: DNA
<213> ORGANISM: Artificial sequence
<220> FEATURE:
<223> OTHER INFORMATION: Synthetic oligomer

<400> SEQUENCE: 38

```
tgtgattggt gttgttgaat ccggtag                                27
```

<210> SEQ ID NO 39
<211> LENGTH: 27
<212> TYPE: DNA
<213> ORGANISM: Artificial sequence
<220> FEATURE:
<223> OTHER INFORMATION: Synthetic oligomer

<400> SEQUENCE: 39

```
tgtgattggt rttgttgaat ccggtag                                27
```

<210> SEQ ID NO 40
<211> LENGTH: 23
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (16)..(16)
<223> OTHER INFORMATION: n is u

<400> SEQUENCE: 40

```
aaagcaggtt gaagangtat atg                                    23
```

<210> SEQ ID NO 41
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature

```
<222> LOCATION: (1)..(25)
<223> OTHER INFORMATION: n is u

<400> SEQUENCE: 41
ngnganngyn gnngnngaan ccggnag                                    27

<210> SEQ ID NO 42
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (1)..(25)
<223> OTHER INFORMATION: n is u

<400> SEQUENCE: 42
ngnganngyn rnngnngaan ccggnag                                    27

<210> SEQ ID NO 43
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (5)..(26)
<223> OTHER INFORMATION: n is u

<400> SEQUENCE: 43
acacnaacca caacaacnna ggccanc                                    27

<210> SEQ ID NO 44
<211> LENGTH: 23
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (19)..(19)
<223> OTHER INFORMATION: n is u

<400> SEQUENCE: 44
aaatgagtcc aaccgaacna atc                                        23

<210> SEQ ID NO 45
<211> LENGTH: 27
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (5)..(26)
<223> OTHER INFORMATION: n is u

<400> SEQUENCE: 45
acacnaacca aaacaacnna ggccanc                                    27

<210> SEQ ID NO 46
<211> LENGTH: 26
<212> TYPE: DNA
<213> ORGANISM: Artificial sequence
<220> FEATURE:
<223> OTHER INFORMATION: Synthetic oligomer
```

<400> SEQUENCE: 46
agcataattt tgtcaacttt yccytc                                       26

<210> SEQ ID NO 47
<211> LENGTH: 30
<212> TYPE: DNA
<213> ORGANISM: Artificial sequence
<220> FEATURE:
<223> OTHER INFORMATION: Synthetic oligomer

<400> SEQUENCE: 47
cattytttgt ttgctgaatt rtrttttgag                                   30

<210> SEQ ID NO 48
<211> LENGTH: 21
<212> TYPE: DNA
<213> ORGANISM: Artificial sequence
<220> FEATURE:
<223> OTHER INFORMATION: Synthetic oligomer

<400> SEQUENCE: 48
ctcaattgtk gmaagtgarc c                                            21

<210> SEQ ID NO 49
<211> LENGTH: 28
<212> TYPE: DNA
<213> ORGANISM: Artificial sequence
<220> FEATURE:
<223> OTHER INFORMATION: Synthetic oligomer

<400> SEQUENCE: 49
ccattatttt cattgtygtr attargcc                                     28

<210> SEQ ID NO 50
<211> LENGTH: 23
<212> TYPE: DNA
<213> ORGANISM: Artificial sequence
<220> FEATURE:
<223> OTHER INFORMATION: Synthetic oligomer

<400> SEQUENCE: 50
cttactttkg atgggactcc rgg                                          23

<210> SEQ ID NO 51
<211> LENGTH: 28
<212> TYPE: DNA
<213> ORGANISM: Artificial sequence
<220> FEATURE:
<223> OTHER INFORMATION: Synthetic oligomer

<400> SEQUENCE: 51
caagtgtaat tgtattgtct tgatcaac                                     28

<210> SEQ ID NO 52
<211> LENGTH: 23
<212> TYPE: DNA
<213> ORGANISM: Artificial sequence
<220> FEATURE:
<223> OTHER INFORMATION: Synthetic oligomer

<400> SEQUENCE: 52
gttccagaya asatgggtct tgc                                          23

<210> SEQ ID NO 53
<211> LENGTH: 23

<212> TYPE: DNA
<213> ORGANISM: Artificial sequence
<220> FEATURE:
<223> OTHER INFORMATION: Synthetic oligomer

<400> SEQUENCE: 53
gacytcaaga agrccagttt gag                                    23

<210> SEQ ID NO 54
<211> LENGTH: 27
<212> TYPE: DNA
<213> ORGANISM: Artificial sequence
<220> FEATURE:
<223> OTHER INFORMATION: Synthetic oligomer

<400> SEQUENCE: 54
cagctatttc yaatgsrtca tcaggag                                27

<210> SEQ ID NO 55
<211> LENGTH: 31
<212> TYPE: DNA
<213> ORGANISM: Artificial sequence
<220> FEATURE:
<223> OTHER INFORMATION: Synthetic oligomer

<400> SEQUENCE: 55
cagtgctaaa ttrtctacat aattragyaa g                           31

<210> SEQ ID NO 56
<211> LENGTH: 21
<212> TYPE: DNA
<213> ORGANISM: Artificial sequence
<220> FEATURE:
<223> OTHER INFORMATION: Synthetic oligomer

<400> SEQUENCE: 56
ctggcatctg tttgcagttg a                                      21

<210> SEQ ID NO 57
<211> LENGTH: 26
<212> TYPE: DNA
<213> ORGANISM: Artificial sequence
<220> FEATURE:
<223> OTHER INFORMATION: Synthetic oligomer

<400> SEQUENCE: 57
ctctcstcaa ctgagaaaac atcatg                                 26

<210> SEQ ID NO 58
<211> LENGTH: 23
<212> TYPE: DNA
<213> ORGANISM: Artificial sequence
<220> FEATURE:
<223> OTHER INFORMATION: Synthetic oligomer

<400> SEQUENCE: 58
catagattcr cgsactttcc cyg                                    23

<210> SEQ ID NO 59
<211> LENGTH: 21
<212> TYPE: DNA
<213> ORGANISM: Artificial sequence
<220> FEATURE:
<223> OTHER INFORMATION: Synthetic oligomer

<400> SEQUENCE: 59

```
ctcaattgtk gmaagtgarc c                                              21
```

<210> SEQ ID NO 60
<211> LENGTH: 29
<212> TYPE: DNA
<213> ORGANISM: Artificial sequence
<220> FEATURE:
<223> OTHER INFORMATION: Synthetic oligomer

<400> SEQUENCE: 60

```
cattctcata atrcataaca aytctgcag                                      29
```

<210> SEQ ID NO 61
<211> LENGTH: 28
<212> TYPE: DNA
<213> ORGANISM: Artificial sequence
<220> FEATURE:
<223> OTHER INFORMATION: Synthetic oligomer

<400> SEQUENCE: 61

```
ccattatttt cattgtygtr attargcc                                       28
```

<210> SEQ ID NO 62
<211> LENGTH: 23
<212> TYPE: DNA
<213> ORGANISM: Artificial sequence
<220> FEATURE:
<223> OTHER INFORMATION: Synthetic oligomer

<400> SEQUENCE: 62

```
catagattcr cgsactttcc cyg                                            23
```

<210> SEQ ID NO 63
<211> LENGTH: 24
<212> TYPE: DNA
<213> ORGANISM: Artificial sequence
<220> FEATURE:
<223> OTHER INFORMATION: Synthetic oligomer

<400> SEQUENCE: 63

```
cttgacayga tctcatytgc ttyg                                           24
```

<210> SEQ ID NO 64
<211> LENGTH: 26
<212> TYPE: DNA
<213> ORGANISM: Artificial sequence
<220> FEATURE:
<223> OTHER INFORMATION: Synthetic oligomer

<400> SEQUENCE: 64

```
ccrttytctc traataattt ycctgc                                         26
```

<210> SEQ ID NO 65
<211> LENGTH: 26
<212> TYPE: DNA
<213> ORGANISM: Artificial sequence
<220> FEATURE:
<223> OTHER INFORMATION: Synthetic oligomer

<400> SEQUENCE: 65

```
catgatgttt tctcagttga wgagag                                         26
```

<210> SEQ ID NO 66
<211> LENGTH: 21
<212> TYPE: DNA
<213> ORGANISM: Artificial sequence

```
<220> FEATURE:
<223> OTHER INFORMATION: Synthetic oligomer

<400> SEQUENCE: 66
cargaaagag gcytgggtta c                                              21

<210> SEQ ID NO 67
<211> LENGTH: 29
<212> TYPE: DNA
<213> ORGANISM: Artificial sequence
<220> FEATURE:
<223> OTHER INFORMATION: Synthetic oligomer

<400> SEQUENCE: 67
ctgcagartt gttatgyatt atgagaatg                                      29

<210> SEQ ID NO 68
<211> LENGTH: 27
<212> TYPE: DNA
<213> ORGANISM: Artificial sequence
<220> FEATURE:
<223> OTHER INFORMATION: Synthetic oligomer

<400> SEQUENCE: 68
gaagtrgcay traaatactg gaaatgg                                        27

<210> SEQ ID NO 69
<211> LENGTH: 26
<212> TYPE: DNA
<213> ORGANISM: Artificial sequence
<220> FEATURE:
<223> OTHER INFORMATION: Synthetic oligomer

<400> SEQUENCE: 69
garggraaag ttgacaaaat tatgct                                         26

<210> SEQ ID NO 70
<211> LENGTH: 30
<212> TYPE: DNA
<213> ORGANISM: Artificial sequence
<220> FEATURE:
<223> OTHER INFORMATION: Synthetic oligomer

<400> SEQUENCE: 70
ctcaaaayay aattcagcaa acaaaraatg                                     30

<210> SEQ ID NO 71
<211> LENGTH: 28
<212> TYPE: DNA
<213> ORGANISM: Artificial sequence
<220> FEATURE:
<223> OTHER INFORMATION: Synthetic oligomer

<400> SEQUENCE: 71
atcaacccac tggatctgaa gagagaag                                       28

<210> SEQ ID NO 72
<211> LENGTH: 21
<212> TYPE: DNA
<213> ORGANISM: Artificial sequence
<220> FEATURE:
<223> OTHER INFORMATION: Synthetic oligomer

<400> SEQUENCE: 72
ggytcacttk cmacaattga g                                              21
```

<210> SEQ ID NO 73
<211> LENGTH: 28
<212> TYPE: DNA
<213> ORGANISM: Artificial sequence
<220> FEATURE:
<223> OTHER INFORMATION: Synthetic oligomer

<400> SEQUENCE: 73
ggcytaatya cracaatgaa ataatgg                                28

<210> SEQ ID NO 74
<211> LENGTH: 22
<212> TYPE: DNA
<213> ORGANISM: Artificial sequence
<220> FEATURE:
<223> OTHER INFORMATION: Synthetic oligomer

<400> SEQUENCE: 74
aaagaattag gtgcaaccar tc                                    22

<210> SEQ ID NO 75
<211> LENGTH: 21
<212> TYPE: DNA
<213> ORGANISM: Artificial sequence
<220> FEATURE:
<223> OTHER INFORMATION: Synthetic oligomer

<400> SEQUENCE: 75
gctgcttatg ggaycagaca c                                     21

<210> SEQ ID NO 76
<211> LENGTH: 23
<212> TYPE: DNA
<213> ORGANISM: Artificial sequence
<220> FEATURE:
<223> OTHER INFORMATION: Synthetic oligomer

<400> SEQUENCE: 76
crgggaaagt wcgygaatct atg                                   23

<210> SEQ ID NO 77
<211> LENGTH: 24
<212> TYPE: DNA
<213> ORGANISM: Artificial sequence
<220> FEATURE:
<223> OTHER INFORMATION: Synthetic oligomer

<400> SEQUENCE: 77
gtccrtcaaa gacytatcaa ggac                                  24

<210> SEQ ID NO 78
<211> LENGTH: 24
<212> TYPE: DNA
<213> ORGANISM: Artificial sequence
<220> FEATURE:
<223> OTHER INFORMATION: Synthetic oligomer

<400> SEQUENCE: 78
aatacaggtt tggataatgg tgtg                                  24

<210> SEQ ID NO 79
<211> LENGTH: 23
<212> TYPE: DNA
<213> ORGANISM: Artificial sequence
<220> FEATURE:
<223> OTHER INFORMATION: Synthetic oligomer

```
<400> SEQUENCE: 79
cctgaagatc ttggaccyyt atc                                           23

<210> SEQ ID NO 80
<211> LENGTH: 23
<212> TYPE: DNA
<213> ORGANISM: Artificial sequence
<220> FEATURE:
<223> OTHER INFORMATION: Synthetic oligomer

<400> SEQUENCE: 80
ccctcattga grgagrtaga ycc                                           23

<210> SEQ ID NO 81
<211> LENGTH: 21
<212> TYPE: DNA
<213> ORGANISM: Artificial sequence
<220> FEATURE:
<223> OTHER INFORMATION: Synthetic oligomer

<400> SEQUENCE: 81
gtattggcca cgacctcttc a                                             21

<210> SEQ ID NO 82
<211> LENGTH: 21
<212> TYPE: DNA
<213> ORGANISM: Artificial sequence
<220> FEATURE:
<223> OTHER INFORMATION: Synthetic oligomer

<400> SEQUENCE: 82
tattggccac gacctcttca g                                             21

<210> SEQ ID NO 83
<211> LENGTH: 29
<212> TYPE: DNA
<213> ORGANISM: Artificial sequence
<220> FEATURE:
<223> OTHER INFORMATION: Synthetic oligomer

<400> SEQUENCE: 83
caaggaaaga yttatttacw agtgctagg                                     29

<210> SEQ ID NO 84
<211> LENGTH: 27
<212> TYPE: DNA
<213> ORGANISM: Artificial sequence
<220> FEATURE:
<223> OTHER INFORMATION: Synthetic oligomer

<400> SEQUENCE: 84
gaatcrarct ggaayaagaa tcattgg                                       27

<210> SEQ ID NO 85
<211> LENGTH: 23
<212> TYPE: DNA
<213> ORGANISM: Artificial sequence
<220> FEATURE:
<223> OTHER INFORMATION: Synthetic oligomer

<400> SEQUENCE: 85
ctcaaactgg ycttcttgar gtc                                           23

<210> SEQ ID NO 86
```

```
<211> LENGTH: 31
<212> TYPE: DNA
<213> ORGANISM: Artificial sequence
<220> FEATURE:
<223> OTHER INFORMATION: Synthetic oligomer

<400> SEQUENCE: 86
cttrctyaat tatgtagaya atttagcact g                              31

<210> SEQ ID NO 87
<211> LENGTH: 21
<212> TYPE: DNA
<213> ORGANISM: Artificial sequence
<220> FEATURE:
<223> OTHER INFORMATION: Synthetic oligomer

<400> SEQUENCE: 87
ggytcacttk cmacaattga g                                         21

<210> SEQ ID NO 88
<211> LENGTH: 24
<212> TYPE: DNA
<213> ORGANISM: Artificial sequence
<220> FEATURE:
<223> OTHER INFORMATION: Synthetic oligomer

<400> SEQUENCE: 88
ccrtcaaaga cytatcaagg actc                                      24

<210> SEQ ID NO 89
<211> LENGTH: 27
<212> TYPE: DNA
<213> ORGANISM: Artificial sequence
<220> FEATURE:
<223> OTHER INFORMATION: Synthetic oligomer

<400> SEQUENCE: 89
caaggactca ttcttgatgc aaaraag                                   27

<210> SEQ ID NO 90
<211> LENGTH: 26
<212> TYPE: DNA
<213> ORGANISM: Artificial sequence
<220> FEATURE:
<223> OTHER INFORMATION: Synthetic oligomer

<400> SEQUENCE: 90
agcataattt tgtcaacttt yccytc                                    26

<210> SEQ ID NO 91
<211> LENGTH: 30
<212> TYPE: DNA
<213> ORGANISM: Artificial sequence
<220> FEATURE:
<223> OTHER INFORMATION: Synthetic oligomer

<400> SEQUENCE: 91
cattytttgt ttgctgaatt rtrttttgag                                30

<210> SEQ ID NO 92
<211> LENGTH: 26
<212> TYPE: DNA
<213> ORGANISM: Artificial sequence
<220> FEATURE:
<223> OTHER INFORMATION: Synthetic oligomer

<400> SEQUENCE: 92
```

```
ctctcstcaa ctgagaaaac atcatg                                          26
```

<210> SEQ ID NO 93
<211> LENGTH: 23
<212> TYPE: DNA
<213> ORGANISM: Artificial sequence
<220> FEATURE:
<223> OTHER INFORMATION: Synthetic oligomer

<400> SEQUENCE: 93

```
cttactttkg atgggactcc rgg                                             23
```

<210> SEQ ID NO 94
<211> LENGTH: 27
<212> TYPE: DNA
<213> ORGANISM: Artificial sequence
<220> FEATURE:
<223> OTHER INFORMATION: Synthetic oligomer

<400> SEQUENCE: 94

```
ccatttccag tatttyartg cyacttc                                         27
```

<210> SEQ ID NO 95
<211> LENGTH: 28
<212> TYPE: DNA
<213> ORGANISM: Artificial sequence
<220> FEATURE:
<223> OTHER INFORMATION: Synthetic oligomer

<400> SEQUENCE: 95

```
caagtgtaat tgtattgtct tgatcaac                                        28
```

<210> SEQ ID NO 96
<211> LENGTH: 23
<212> TYPE: DNA
<213> ORGANISM: Artificial sequence
<220> FEATURE:
<223> OTHER INFORMATION: Synthetic oligomer

<400> SEQUENCE: 96

```
gttccagaya asatgggtct tgc                                             23
```

<210> SEQ ID NO 97
<211> LENGTH: 23
<212> TYPE: DNA
<213> ORGANISM: Artificial sequence
<220> FEATURE:
<223> OTHER INFORMATION: Synthetic oligomer

<400> SEQUENCE: 97

```
cctgaagatc ttggaccyyt atc                                             23
```

<210> SEQ ID NO 98
<211> LENGTH: 23
<212> TYPE: DNA
<213> ORGANISM: Artificial sequence
<220> FEATURE:
<223> OTHER INFORMATION: Synthetic oligomer

<400> SEQUENCE: 98

```
ccctcattga grgagrtaga ycc                                             23
```

<210> SEQ ID NO 99
<211> LENGTH: 21
<212> TYPE: DNA

<210> SEQ ID NO 99
<211> LENGTH: 21
<212> TYPE: DNA
<213> ORGANISM: Artificial sequence
<220> FEATURE:
<223> OTHER INFORMATION: Synthetic oligomer

<400> SEQUENCE: 99
gtattggcca cgacctcttc a                                        21

<210> SEQ ID NO 100
<211> LENGTH: 21
<212> TYPE: DNA
<213> ORGANISM: Artificial sequence
<220> FEATURE:
<223> OTHER INFORMATION: Synthetic oligomer

<400> SEQUENCE: 100
tattggccac gacctcttca g                                        21

<210> SEQ ID NO 101
<211> LENGTH: 29
<212> TYPE: DNA
<213> ORGANISM: Artificial sequence
<220> FEATURE:
<223> OTHER INFORMATION: Synthetic oligomer

<400> SEQUENCE: 101
caaggaaaga yttatttacw agtgctagg                                29

<210> SEQ ID NO 102
<211> LENGTH: 27
<212> TYPE: DNA
<213> ORGANISM: Artificial sequence
<220> FEATURE:
<223> OTHER INFORMATION: Synthetic oligomer

<400> SEQUENCE: 102
gaatcrarct ggaayaagaa tcattgg                                  27

<210> SEQ ID NO 103
<211> LENGTH: 23
<212> TYPE: DNA
<213> ORGANISM: Artificial sequence
<220> FEATURE:
<223> OTHER INFORMATION: Synthetic oligomer

<400> SEQUENCE: 103
ctcaaactgg ycttcttgar gtc                                      23

<210> SEQ ID NO 104
<211> LENGTH: 31
<212> TYPE: DNA
<213> ORGANISM: Artificial sequence
<220> FEATURE:
<223> OTHER INFORMATION: Synthetic oligomer

<400> SEQUENCE: 104
cttrctyaat tatgtagaya atttagcact g                             31

<210> SEQ ID NO 105
<211> LENGTH: 26
<212> TYPE: DNA
<213> ORGANISM: Artificial sequence
<220> FEATURE:
<223> OTHER INFORMATION: Synthetic oligomer

<400> SEQUENCE: 105
catgatgttt tctcagttga wgagag                                   26

<210> SEQ ID NO 106
<211> LENGTH: 29
<212> TYPE: DNA
<213> ORGANISM: Artificial sequence
<220> FEATURE:
<223> OTHER INFORMATION: Synthetic oligomer

<400> SEQUENCE: 106
ctgcagartt gttatgyatt atgagaatg                                            29

<210> SEQ ID NO 107
<211> LENGTH: 23
<212> TYPE: DNA
<213> ORGANISM: Artificial sequence
<220> FEATURE:
<223> OTHER INFORMATION: Synthetic oligomer

<400> SEQUENCE: 107
crgggaaagt wcgygaatct atg                                                  23

<210> SEQ ID NO 108
<211> LENGTH: 27
<212> TYPE: DNA
<213> ORGANISM: Artificial sequence
<220> FEATURE:
<223> OTHER INFORMATION: Synthetic oligomer

<400> SEQUENCE: 108
gaagtrgcay traaatactg gaaatgg                                              27

<210> SEQ ID NO 109
<211> LENGTH: 23
<212> TYPE: DNA
<213> ORGANISM: Artificial sequence
<220> FEATURE:
<223> OTHER INFORMATION: Synthetic oligomer

<400> SEQUENCE: 109
gacytcaaga agrccagttt gag                                                  23

<210> SEQ ID NO 110
<211> LENGTH: 31
<212> TYPE: DNA
<213> ORGANISM: Artificial sequence
<220> FEATURE:
<223> OTHER INFORMATION: Synthetic oligomer

<400> SEQUENCE: 110
cagtgctaaa ttrtctacat aattragyaa g                                         31

<210> SEQ ID NO 111
<211> LENGTH: 29
<212> TYPE: DNA
<213> ORGANISM: Artificial sequence
<220> FEATURE:
<223> OTHER INFORMATION: Synthetic oligomer

<400> SEQUENCE: 111
cattctcata atrcataaca aytctgcag                                            29

<210> SEQ ID NO 112
<211> LENGTH: 27
<212> TYPE: DNA
<213> ORGANISM: Artificial sequence
<220> FEATURE:

<223> OTHER INFORMATION: Synthetic oligomer

<400> SEQUENCE: 112
ccatttccag tatttyartg cyacttc                                               27

<210> SEQ ID NO 113
<211> LENGTH: 24
<212> TYPE: DNA
<213> ORGANISM: Artificial sequence
<220> FEATURE:
<223> OTHER INFORMATION: Synthetic oligomer

<400> SEQUENCE: 113
cttgacayga tctcatytgc ttyg                                                  24

<210> SEQ ID NO 114
<211> LENGTH: 26
<212> TYPE: DNA
<213> ORGANISM: Artificial sequence
<220> FEATURE:
<223> OTHER INFORMATION: Synthetic oligomer

<400> SEQUENCE: 114
ccrttytctc traataattt ycctgc                                                26

<210> SEQ ID NO 115
<211> LENGTH: 27
<212> TYPE: DNA
<213> ORGANISM: Artificial sequence
<220> FEATURE:
<223> OTHER INFORMATION: Synthetic oligomer

<400> SEQUENCE: 115
cagctatttc yaatgsrtca tcaggag                                               27

<210> SEQ ID NO 116
<211> LENGTH: 26
<212> TYPE: DNA
<213> ORGANISM: Artificial sequence
<220> FEATURE:
<223> OTHER INFORMATION: Synthetic oligomer

<400> SEQUENCE: 116
garggraaag ttgacaaaat tatgct                                                26

<210> SEQ ID NO 117
<211> LENGTH: 30
<212> TYPE: DNA
<213> ORGANISM: Artificial sequence
<220> FEATURE:
<223> OTHER INFORMATION: Synthetic oligomer

<400> SEQUENCE: 117
ctcaaaayay aattcagcaa acaaaraatg                                            30

<210> SEQ ID NO 118
<211> LENGTH: 28
<212> TYPE: DNA
<213> ORGANISM: Artificial sequence
<220> FEATURE:
<223> OTHER INFORMATION: Synthetic oligomer

<400> SEQUENCE: 118
ggcytaatya cracaatgaa aataatgg                                              28

```
<210> SEQ ID NO 119
<211> LENGTH: 22
<212> TYPE: DNA
<213> ORGANISM: Artificial sequence
<220> FEATURE:
<223> OTHER INFORMATION: Synthetic oligomer

<400> SEQUENCE: 119
aaagaattag gtgcaaccar tc                                              22

<210> SEQ ID NO 120
<211> LENGTH: 21
<212> TYPE: DNA
<213> ORGANISM: Artificial sequence
<220> FEATURE:
<223> OTHER INFORMATION: Synthetic oligomer

<400> SEQUENCE: 120
gctgcttatg ggaycagaca c                                               21

<210> SEQ ID NO 121
<211> LENGTH: 24
<212> TYPE: DNA
<213> ORGANISM: Artificial sequence
<220> FEATURE:
<223> OTHER INFORMATION: Synthetic oligomer

<400> SEQUENCE: 121
gtccrtcaaa gacytatcaa ggac                                            24

<210> SEQ ID NO 122
<211> LENGTH: 24
<212> TYPE: DNA
<213> ORGANISM: Artificial sequence
<220> FEATURE:
<223> OTHER INFORMATION: Synthetic oligomer

<400> SEQUENCE: 122
ccrtcaaaga cytatcaagg actc                                            24

<210> SEQ ID NO 123
<211> LENGTH: 27
<212> TYPE: DNA
<213> ORGANISM: Artificial sequence
<220> FEATURE:
<223> OTHER INFORMATION: Synthetic oligomer

<400> SEQUENCE: 123
caaggactca ttcttgatgc aaaraag                                         27

<210> SEQ ID NO 124
<211> LENGTH: 21
<212> TYPE: DNA
<213> ORGANISM: Artificial sequence
<220> FEATURE:
<223> OTHER INFORMATION: Synthetic oligomer

<400> SEQUENCE: 124
cargaaagag gcytgggtta c                                               21

<210> SEQ ID NO 125
<211> LENGTH: 37
<212> TYPE: DNA
<213> ORGANISM: Artificial sequence
<220> FEATURE:
<223> OTHER INFORMATION: Synthetic oligomer
<220> FEATURE:
```

```
<221> NAME/KEY: misc_feature
<222> LOCATION: (10)..(10)
<223> OTHER INFORMATION: n is u

<400> SEQUENCE: 125
cagagatctn acacaattaa tagagaagtc atgcaac                    37
```